US011227670B2

(12) United States Patent
Serber et al.

(10) Patent No.: US 11,227,670 B2
(45) Date of Patent: Jan. 18, 2022

(54) MICROBIAL ENGINEERING METHODS AND SYSTEMS FOR OPTIMIZING MICROBE FITNESS

(71) Applicant: ZYMERGEN INC., Emeryville, CA (US)

(72) Inventors: William Serber, Berkeley, CA (US); Erik Jedediah Dean, Lafayette, CA (US)

(73) Assignee: ZYMERGEN INC., Emeryville, CA (US)

( * ) Notice: Subject to any disclaimer, the term of this patent is extended or adjusted under 35 U.S.C. 154(b) by 245 days.

(21) Appl. No.: 16/609,360

(22) PCT Filed: May 4, 2018

(86) PCT No.: PCT/US2018/031258
§ 371 (c)(1),
(2) Date: Oct. 29, 2019

(87) PCT Pub. No.: WO2018/204890
PCT Pub. Date: Nov. 8, 2018

(65) Prior Publication Data
US 2020/0173900 A1  Jun. 4, 2020

Related U.S. Application Data

(60) Provisional application No. 62/502,495, filed on May 5, 2017.

(51) Int. Cl.
*G06K 9/00* (2006.01)
*G16B 50/00* (2019.01)
(Continued)

(52) U.S. Cl.
CPC ......... *G16B 50/00* (2019.02); *G01N 15/0227* (2013.01); *G06T 7/0004* (2013.01); *G06T 2207/10056* (2013.01)

(58) Field of Classification Search
None
See application file for complete search history.

(56) References Cited

U.S. PATENT DOCUMENTS 6,071,748 A   6/2000 Modlin et al.
6,243,486 B1  6/2001 Weiss
(Continued)

OTHER PUBLICATIONS

Banks et al., A Quantitative Fitness Analysis Workflow, 2012, Journal of Visualized Experiments, doi:10.3791/4018, pp. 1-7, AAPA furnished via ISR/IDS.*
(Continued)

*Primary Examiner* — Guillermo M Rivera-Martinez
(74) *Attorney, Agent, or Firm* — Almanac IP Advisors LLP

(57) ABSTRACT

The present disclosure provides a microbe engineering platform that permits optimization of microbe fitness levels to optimize a microbe's suitability for industrial fermentation. The disclosed platform identifies an association between microbe properties and microbe fitness levels. The association between microbe properties and microbe fitness levels may be used to identify candidate microbes with desired fitness levels. The identified candidate microbes may be used to further optimize the industrial fermentation process.

20 Claims, 9 Drawing Sheets

(51) Int. Cl.
*G01N 15/02* (2006.01)
*G06T 7/00* (2017.01)

(56) References Cited

U.S. PATENT DOCUMENTS

| | | | | |
|---|---|---|---|---|
| 8,094,916 | B2* | 1/2012 | Graessle | G01N 15/1475 |
| | | | | 382/133 |
| 2004/0092001 | A1* | 5/2004 | Bedingham | C12M 23/04 |
| | | | | 435/286.2 |
| 2004/0253660 | A1* | 12/2004 | Gibbs | C12Q 1/045 |
| | | | | 435/34 |
| 2005/0069934 | A1* | 3/2005 | Berka | C12Q 1/6895 |
| | | | | 435/6.13 |
| 2006/0166305 | A1 | 7/2006 | Jiang et al. | |
| 2007/0037220 | A1 | 2/2007 | Burke et al. | |
| 2010/0062442 | A1 | 3/2010 | Burke et al. | |
| 2010/0074507 | A1 | 3/2010 | Klottrup et al. | |
| 2012/0028239 | A1 | 2/2012 | Richmond et al. | |
| 2012/0082361 | A1 | 4/2012 | Burke et al. | |
| 2014/0170708 | A1* | 6/2014 | Zieler | C07H 21/02 |
| | | | | 435/91.2 |
| 2015/0284811 | A1* | 10/2015 | Knight | E21B 49/086 |
| | | | | 506/2 |
| 2015/0339510 | A1* | 11/2015 | Bolea | G06K 9/00147 |
| | | | | 382/133 |
| 2016/0311877 | A1* | 10/2016 | Watters | G01N 33/6854 |

OTHER PUBLICATIONS

Claim amendment in European patent application No. 18737440.0 filed on Dec. 3, 2019, 4 pages.
Claim amendment in European patent application No. 18737440.0 filed on Dec. 4, 2019, 4 pages.
Application of European patent application No. 18737440.0 filed on Dec. 3, 2019, 5 pages.
International Search Report for PCT/US2018/031258 dated Aug. 13, 2018, 4 pages.
Written Opinion for PCT/US2018/031258 dated Aug. 13, 2018, 11 pages.
"A Quantitative Fitness Analysis Workflow," Banks, et al, Journal of Visualized Experiments, No. 66, Aug. 2012, 7 pages.
"Colonyzer: automated quantification of micro-organism growth characteristics on solid agar," Lawless, et al, BMC Bioinformatics, vol. 11, No. 1, Jan. 2010, 12 pages.
"Fluorescent Bacterial Colony Selection Using QPix 400 Systems," Molecular Devices Application Note, copyrighted 2015, 3 pages. Downloaded from: https://www.moleculardevices.com/en/assets/app-note/biologics/fluorescent-bacterial-colony-selection-using-qpix-400-system.
"Automated colorimetric colony selection: Blue-white colony screening with QPix 400 Series," Molecular Devices Application Note, copyrighted 2015, 3 pages. Downloaded from: https://www.moleculardevices.com/en/assets/app-note/biologics/automated-colorimetric-colony-selection-blue-white-colony-screening-with-qpix-400-series.
"Expanded fluorescence screening using QPix 400 series," Molecular Devices Application Note, copyrighted 2016, 3 pages. Downloaded from: https://www.moleculardevices.com/en/assets/app-note/biologics/expanded-fluorescence-screening-using-qpix-400-series.
"Not just *E. coli*—Efficient, automated microbial colony transfer for a wide variety of microorganisms," Molecular devices, copyrighted 2016, 2 pages. Downloaded from: https://www.moleculardevices.com/sites/default/files/en/assets/data-sheets/biologics/qpix-400-series-organism-specific-picking-pins-and-detection-software.pdf.
"Validation of next generation microbial colony pickers using fluorescence in a complete workflow solution," Molecular Devices, copyrighted 2013, 1 page. Downloaded from: https://www.moleculardevices.com/sites/default/files/en/assets/scientific-posters/biologics/microbial-colony-pickers-qpix-series-complete-workflow.pdf.

* cited by examiner

MICROBIAL ENGINEERING METHODS AND SYSTEMS FOR OPTIMIZING MICROBE FITNESS

CROSS-REFERENCE TO RELATED APPLICATIONS

This application is a national stage entry of International PCT Application No. PCT/US2018/031258, filed on May 4, 2018, which claims benefit of priority to U.S. provisional application No. 62/502,495, filed on May 5, 2017, both of which are hereby incorporated by reference in their entirety, including all descriptions, references, figures, and claims for all purposes.

FIELD

The present disclosure is directed to identifying microorganisms with desired fitness levels, and, in particular, identifying microorganisms with desired fitness levels by considering one or more data properties such as properties of an image of the microorganism.

BACKGROUND

Microorganisms can be used to produce many industrial compounds. Arriving at a strain which produces a compound at a commercially viable scale can, however, be a cumbersome and time-consuming process which involves analyzing multiple microbes over one or more generations. Microbes produced in one generation may be analyzed to select the candidates most fit for production of a desired product. Those candidates may then be subjected to numerous mutations to produce another generation of microbes. The new generation may similarly be analyzed for yield, productivity, and other properties to select candidates for the next round of analysis, gene modification, or product synthesis. The process may continue in an iterative manner to improve microbe fitness.

One step in the process that can be particularly inefficient is analysis of the properties of the microbes to determine which microbes should be carried forward into future generations for further development. Methods to automate the selection of microbes from one generation to the next could greatly facilitate the ability to speed the production of high fitness microbes.

SUMMARY OF THE DISCLOSURE

Embodiments of the present disclosure provide microbial engineering processes and systems that permit optimization of microbe fitness levels to optimize a microbe's suitability for industrial fermentation. To improve fermentation efficiency, in some embodiments, the microbe fitness levels to be optimized may be related to one or more of: product yield, productivity, or titer. In some embodiments, microbe fitness levels to be optimized may be related to microbe process tolerance. Optimization of microbe process tolerance may include increasing the microbe tolerance to variations in process parameters (e.g., pH, or temperature) encountered during the growth of microbes or during manufacturing of products using the microbes. Optimization of microbe process tolerance may include increasing the microbe resistance to contamination or mutation.

In embodiments of the disclosure, the microbial engineering processes and systems permit rapid improvements in microbe fitness levels by iterating on identified associations between microbe appearance (e.g., microbe colony size, fluorescence data) and microbe fitness levels. In many instances, the availability of microbe characterization equipment leads to shorter time required to determine microbe appearance compared to the time required to determine microbe fitness levels. Using microbe appearance and the identified association between microbe appearance and microbe fitness levels leads to a quicker path to microbe selection or production process improvements.

Embodiments of the present disclosure include identification of a collection of microbes with variable fitness. Systems, methods, and computer readable media are described herein that: obtain data relating to a plurality of collections of microbes, wherein one or more collections of microbes has a different fitness than at least one other collection of microbes; determine one or more data properties of each collection of microbes in a first set of the plurality of collections of microbes based at least in part upon the data; determine an expressed fitness of each collection of microbes in the first set; and identify an association between the determined one or more data properties and expressed fitness level of one or more collections of microbes in the first set. In some embodiments, the collections of microbes may be individual microbes, groups of microbes, or microbe colonies. In some embodiments, the obtained data may be related to the appearance of the collections of microbes. In some embodiments, the obtained data may be image data and the data properties may be image properties. In some embodiments, the identified association may be used to select collections of microbes for further processing.

Embodiments of the present disclosure include predicting the fitness level of a collection of microbes. Systems, methods, and computer readable media are described herein that: obtain data relating to a collection of microbes; determine one or more data properties of the collection of microbes based at least in part upon the data; and determine the predicted fitness level for the collection of microbes based at least in part upon an association relating the determined data properties and the fitness level.

DETAILED DESCRIPTION

Definitions

Figure 1:
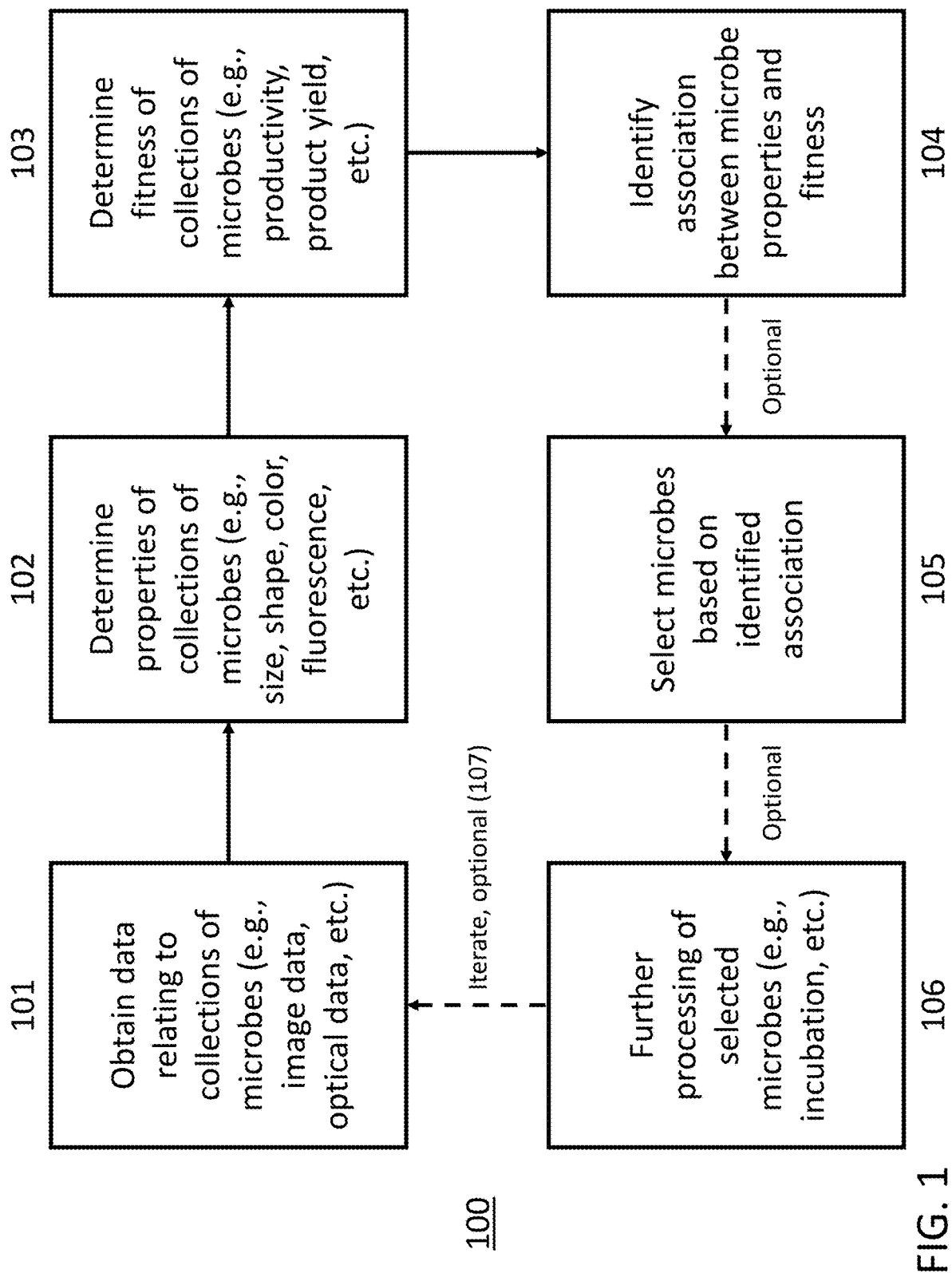
FIG. 1 depicts an exemplary process flow according to embodiments of the present disclosure. The depicted process includes optional steps that permit iterative learning based on the disclosed process flow.

As used herein the terms "microbe" "cellular organism" or "microorganism" should be taken broadly. These terms are used interchangeably and include, but are not limited to, the two prokaryotic domains, Bacteria and Archaea, as well as eukaryotic organisms, including mammalian cells, fungi, and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in those tables or figures. The same characterization holds true for the recitation of these terms in other parts of the Specification, such as in the Examples.

The term "prokaryotes" is recognized in the art and refers to cells which contain no nucleus or other membrane-bound cellular organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

In some embodiments, productivity may be volumetric productivity. The term "volumetric productivity" or "production rate" is defined as the amount of product formed per volume of medium per unit of time. Volumetric productivity can be reported in gram per liter per hour (g/L/h).

In some embodiments, productivity may be specific productivity. The term "specific productivity" is defined as the rate of formation of the product. Specific productivity is herein further defined as the specific productivity in gram product per gram of cell dry weight (CDW) per hour (g/g CDW/h). Using the relation of CDW to $OD_{600}$ for the given microorganism, specific productivity can also be expressed as gram product per liter culture medium per optical density of the culture broth at 600 nm ($OD_{600}$) per hour (g/L/h/$OD_{600}$).

In some embodiments, titer may be total titer. The term "total titer" is defined as the sum of all product of interest produced in a process, including but not limited to the product of interest in solution, the product of interest in gas phase if applicable, and any product of interest removed from the process and recovered relative to the initial volume in the process or the operating volume in the process.

In some embodiments, "yield," as in product yield, is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product.

Description

The present description is made with reference to the accompanying drawings, in which various example embodiments are shown. However, many different example embodiments may be used, and thus the description should not be construed as limited to the example embodiments set forth herein. Rather, these example embodiments are provided so that this disclosure will be thorough and complete. Various modifications to the exemplary embodiments will be readily apparent to those skilled in the art, and the generic principles defined herein may be applied to other embodiments and applications without departing from the spirit and scope of the disclosure. Thus, the present disclosure is not intended to be limited to the embodiments shown, but is to be accorded the widest scope consistent with the principles and features disclosed herein.

In embodiments, the microbial engineering platform disclosed herein allows for rapid improvements in microbe fitness by iterating on identified associations between microbe appearance and fitness level. As discussed above, the time and effort required to identify microbes with improved fitness (e.g., industrial performance) is very large due to requirements of the microbe performance detection, measurement, or quantification processes. In many cases, the process to identify microbes with improved industrial performance is hindered by multiple factors. First, improvements in the industrial performance appear in small increments, for example, improvements in productivity or product yield may appear in the range below about 5% or in the range below about 1%. Second, detection of a small industrial performance improvement requires many samples to achieve an acceptable signal-to-noise ratio (SNR), e.g., SNR of greater than 2.

To overcome the technical and process challenges that are present in such cases, the embodiments of the disclosure utilize large sample statistics and randomization of sample sets along with identified associations between microbe appearance and fitness levels to reduce the time and effort required to identify microbes that have the potential for industrial improvements. In many cases, the time and effort required to analyze the microbe fitness levels are vastly larger than the time and effort required to characterize the microbe appearance. In some cases, the time and effort required to determine the microbe appearance is reduced due to availability of automated microbe appearance characterization equipment including, for example, the Molecular Devices QPix 400 series microbial colony picker or a Hudson Robotics RapidPick colony picker.

The embodiments of the disclosure utilize sampling of microbe fitness levels with varying appearance values, within one or more appearance value ranges, to identify an association between the fitness levels and microbe appearance. The identified association may be used to select microbes based on appearance, interpolating within the sampled microbe appearance value range or extrapolating outside the sampled microbe appearance value range, to identify microbe candidates with a desired fitness.

In some embodiments, a microbe engineering process obtains image data relating to a plurality of collections of microbes with different fitness levels. One or more image properties of a collection of microbes in a first set of collections of microbes of the plurality of collections of microbes may be determined based at least in part upon the obtained image data. An image property of the one or more image properties may be related to the appearance of a collection of microbes in the first set of collections of microbes. One or more fitness levels of one or more collections of microbes in the first set are determined. An association between the determined one or more image properties and the determined fitness levels may be identified. In some embodiments, the identified association may be used to select a collection of microbes based on their appearance for further processing. In some embodiments, after further processing, the selected collections of microbes may be processed through one or more of the obtaining image data, characterizing one or more image properties, analyzing to determine the fitness levels, and identifying an association between the one or more image properties and fitness levels process steps in an iterative manner to optimize selection of microbes with improved fitness.

In some embodiments, collections of microbes may be excluded from the selection process or may be included in the selection process based on rules. In some embodiments, the rules may require replicates of collections of microbes to improve accuracy of measured data. In some embodiments, the rules may require excluding collections of microbes, e.g., based on one or more image properties, based on other rules, or based on manual selection. In some embodiments, collections of microbes corresponding to process controls may be selected for inclusion in subsequent processing steps. In some embodiments, a collection of microbes may be selected based on its image property data compared to statistical data for image properties of collections of microbes (e.g., at a sample or population level; including or not including the particular collection of microbes). In some embodiments, the statistical data includes at least one or more of: mean, median, or standard deviation of the image property. In some embodiments, collections of microbes may be ranked in an order for selection based on one or more of: one or more image properties, the identified association, or the location on the source labware (e.g., location of well or region in source labware). In some embodiments, collections of microbes may be selected from the ranked list of collections of microbes with more collections of microbes selected from the top of the ranked list than from the lower ranks, e.g., selecting only the top 10 ranked collections of microbes, or selecting the top four ranked collections of microbes from top 8 ranked collections of microbes and the two bottom most ranked collections of microbes. In some embodiments, collections of microbes may be selected to maintain diversity among the collections of microbes in the subsequent steps in the process. In some embodiments, diversity is maintained by including collections of microbes of varying (e.g., high and low) ranks.

In some embodiments, the collection of microbes may be a single microbe. In some embodiments, one or more image properties may be determined based in part upon capturing an image of a single microbe using a microscope. In some embodiments, a given image may include image data for more than one microbe. In some embodiments, the image data for the single microbe may be analyzed to determine image properties related to the microbe size, shape, color, or some other optically identifiable property. In some embodiments, the image data for the single microbe may be analyzed to determine image properties related to subcellular properties of the microbes, for example, identifying organelle or identifying organelle properties. The microbe appearance may be determined by capturing a fluorescence signal (e.g., representing fluorescence intensity, or fluorescence wavelength) from a single microbe in a cell sorter.

In some embodiments, the collection of microbes may be a group of two or more microbes. In some embodiments, the number of microbes in the group may range from two to about 100 microbes. In some embodiments, the collection of microbes may be a group of isogenic microbes. In some embodiments, the collection of microbes may be characterized by imaging the group of microbes using a microscope. In some embodiments, the images of the group of microbes may be analyzed to determine image properties related to the group size, shape, or color. In some embodiments, the images of the group of microbes may be analyzed to determine image properties related to the structural arrangement of two or more microbes in the group, e.g., microbe group packing density (microbes per volume). In some embodiments, the images of the group of microbes may be analyzed to determine image properties related to the subcellular properties of the microbes, for example, identifying organelle or identifying organelle properties. In some embodiments, the images of the group of microbes may be analyzed to determine image properties of single microbes in the group as described above.

In some embodiments, the collection of microbes may be a microbe colony. In some embodiments, the collection of microbes may be a microbe colony comprising a collection of more than one microbe with the collection being made up of isogenic microbes. In some embodiments, the microbe colonies range from about 0.3 mm to about 3 mm diameter in size when grown on labware (e.g., source agar plate). In some embodiments, the microbe colony appearance may be determined using an image of a source agar plate including one or more microbe colonies. In some embodiments, the image of the source agar plate may be analyzed to determine image properties related to the microbe colony size, shape, color, fluorescence, uniformity, opacity, edge sharpness, topology, or height. In some embodiments, the image of the source agar plate may be analyzed to determine, for a given microbe colony, image properties related to the distance to nearest neighboring microbe colony. In some embodiments, the image of the source agar plate may be analyzed to determine, for a given microbe colony, image properties related to the local density of microbe colonies. In some embodiments, the local density of microbe colonies may be determined by counting the number of microbe colonies within a predetermined distance from the given microbe colony. In some embodiments, the microbe colony appearance may be characterized as a growth rate, determined, for example, based on microbe colony size and time elapsed. In some embodiments, the microbe colony growth rate may be determined based on the change of microbe colony size (e.g., using two images of the source agar plate) and the time elapsed (between capturing the two images).

In some embodiments, the image properties of a collection of microbes may be characterized while the microbes are encapsulated in media. In some embodiments, the media may be a droplet formed by a microfluidic device. In addition to characterizing the image properties of a collection of microbes in the droplets using the techniques described above, the appearance of the collection of microbes in the droplets or the products produced by the collection of microbes in droplets may be analyzed by using detectors in a microfluidic system or by carrying out analytical processes using one or more microfluidic systems to determine data related to microbe appearance or microbe fitness levels.

In some embodiments, one or more images of a source plate may be obtained wherein the image includes image data for collections of microbes located in the source plate. In some embodiments, image data from one or more images may be analyzed to determine the image properties of a collection of microbes. In some embodiments, collections of microbes may be selected from the source plate to determine their fitness. In some embodiments, one or more of capturing the images of the collections of microbes on the source plate, characterizing the image properties of the collections of microbes, or selection of a collection of microbes for analysis of microbe fitness may be completed using an automated colony picker, for example, using a Molecular Devices QPix 400 series microbial colony picker or a Hudson Robotics RapidPick colony picker. In some embodiments, a collection of microbes may be selected for incubation based at least in part upon an association between one or more image properties of collections of microbes and fitness level of the collections of microbes.

In some embodiments, the collections of microbes are analyzed to determine fitness level. In some embodiments, the microbe fitness level may be related to product yield. In some embodiments, the product may be selected from one or more categories, the categories including: solvents, plastics, reagents, flavors, fragrances, nutraceuticals (e.g., vitamins, amino acids, etc.), and pharmaceuticals (e.g., antibiotics, statins, etc.). In some embodiments, the product may be: Glutamic Acid, Lysine, Phenylalanine, Threonine, Tryptophan, Vitamin B12, Vitamin B2, Vitamin C, Erythromycin, Tetracyclines, Penicillin G/V, Cephalosporin C, Lovastatin, Simvastatin, Pravastatin, Cyclosporin A, Paclitaxel, Citric Acid, Xanthan Gum, Acetic Acid, Gluconic Acid, Itaconic Acid, Lactic Acid, Polyhydroxyalkanoates (PHA), Beta-Carotene, Formic Acid, Sorbitol, Methionine, Biotin, 1,3 Propanediol (PDO), 1,4 Butanediol (BDO), Acetic Acid, Acrylic Acid, Adipic Acid, Vanillic Acid, Butadiene (BD), Dodecanedioic Acid (DDDA), Isoprene, Malic Acid, Propionic Acid, Sebacic Acid, Succinic Acid, or Acetone, n-Butanol. In some embodiments, the microbe fitness level may be related to productivity. In some embodiments, the microbe fitness level may be related to titer. In some embodiments, the microbe fitness level may be related to tolerance to a production condition. In some embodiments, the production condition may include pH level, or temperature encountered during production. In some embodiments, growth conditions may be controlled while characterizing microbe fitness level. For example, microbes with the greatest fitness level under nutrient-rich conditions may be different from microbes with greatest fitness level under nutrient-limited conditions. A collection of microbes may demonstrate improved fitness by, in energy constrained (e.g., nutrient-limited) conditions, diverting energy resources away from microbe growth to production of a desired product.

In some embodiments, to calculate product yield or productivity, a collection of microbes may be analyzed by running an assay to determine the amount of product or products of interest in a sample broth produced by the microbes. In some embodiments, the microbes may be lysed to produce the sample for the assay. In some embodiments, running the assay comprises sample preparation using techniques such as solvent extraction, derivatization, dilution, or filtration. In some embodiments, running the assay comprises quantification using enzymatic methods or gas or liquid chromatography using a variety of detectors such as fluorescence, light absorption, refractive index, or mass spectroscopy. In some embodiments, the signal derived from the sample may be compared to a known concentration of analyte to quantify the results of the assay.

FIG. 1 shows an exemplary process flow 100 based on an embodiment of the disclosure. The exemplary process flow includes, in step 101, obtaining data relating to the appearance of a plurality of collections of microbes. In some embodiments, the plurality of collections of microbes are of the same species. In some embodiments, at least one collection of microbes in the plurality of collections of microbes has a fitness level that differs from at least one other collection of microbes in the plurality of collections of microbes. In some embodiments, the data relating to a plurality of collections of microbes includes images of a plurality of collections of microbes. In some embodiments, the images of a plurality of collections of microbes includes images of microbe colonies. In some embodiments, the images of a plurality of collections of microbes includes images of one or more individual microbes. In some embodiments, the images of a plurality of collections of microbes includes images of groups of two or more microbes. In some embodiments, the data relating to a plurality of collections of microbes includes optical data relating to the collections of microbes. In some embodiments, the optical data relating to the collections of microbes includes fluorescence data for the collections of microbes.

The exemplary process flow includes, in step 102, determining one or more data properties for each of one or more collections of microbes based on the data relating to one or more collections of microbes. In some embodiments, the data relating to one or more collections of microbes may be image data and the one or more data properties may be one or more image properties. In some embodiments, the one or more image properties may be ascertained directly from the obtained image data by computations performed by one or more computing devices. In some embodiments, one or more computing devices may process the obtained image data to determine the one or more image properties. In some embodiments, the one or more image properties may be determined by a computing device by receiving the corresponding information from another computing device. In some embodiments, determining one or more image properties of one or more collections of microbes includes identifying one or more image properties relating to each collection of microbes based at least in part upon the image data. In some embodiments, the image property relating to collections of microbes may be selected from the list consisting of: size, growth rate, eccentricity, aspect ratio, surface roughness, edge roughness, edge sharpness, color, fluorescence, uniformity, opacity, sharpness, topology, volume, microbe density, microbe group density, microbe colony density, distance to nearest neighboring microbe, distance to nearest neighboring microbe group, distance to nearest neighboring microbe colony, and any combination thereof. In some embodiments, the color image property may be characterized as the intensity level of one or more colors (e.g., red, green, blue, yellow, or white) or signals (e.g., luminance, luma, or chroma) used in the image data. In some embodiments, the size image property may be selected from the list consisting of: microbe collection radius, microbe collection length, microbe collection width, microbe collection height, microbe collection surface area, microbe collection volume, microbe collection cross-sectional area, and any combination thereof.

The exemplary process flow includes, in step 103, determining one or more fitness levels of each collection of microbes from step 102. In some embodiments, the one or more fitness levels of a collection of microbes may be determined by analyzing microbes from the collection of microbes entirely through an automated means, e.g., by analysis equipment. In some embodiments, the one or more fitness levels of a collection of microbes may be determined by analyzing microbes from the collection of microbes manually (e.g., by human implementation) or through a combination of automated and manual means. In some embodiments, the fitness is related to a production metric. In some embodiments, the fitness is related to one or more of: product yield, productivity, titer, or tolerance to a production condition. In some embodiments, the tolerance to a production condition may be selected from the list consisting of: pH tolerance, temperature tolerance, resistance to contamination, resistance to mutation, and any combination thereof. In some embodiments, the product yield or productivity is related to a product selected from the following product categories: solvents, plastics, reagents, flavors, fragrances, nutraceuticals (e.g., vitamins, amino acids, etc.), or pharmaceuticals (e.g., antibiotics, statins, etc.). In some embodiments, the product yield or productivity is related to one of the following products: Glutamic Acid, Lysine, Phenylalanine, Threonine, Tryptophan, Vitamin B12, Vitamin B2, Vitamin C, Erythromycin, Tetracyclines, Penicillin G/V, Cephalosporin C, Lovastatin, Simvastatin, Pravastatin, Cyclosporin A, Paclitaxel, Citric Acid, Xanthan Gum, Acetic Acid, Gluconic Acid, Itaconic Acid, Lactic Acid, Polyhydroxyalkanoates (PHA), Beta-Carotene, Formic Acid, Sorbitol, Methionine, Biotin, 1,3 Propanediol (PDO), 1,4 Butanediol (BDO), Acetic Acid, Acrylic Acid, Adipic Acid, Vanillic Acid, Butadiene (BD), Dodecanedioic Acid (DDDA), Isoprene, Malic Acid, Propionic Acid, Sebacic Acid, Succinic Acid, or Acetone, n-Butanol. In some embodiments, analyzing the fitness level is carried out by running an assay to determine the amount of one or more products of interest in a sample broth. Running an assay may include sample preparation including one or more techniques selected from the list consisting of: solvent extraction, derivatization, dilution and filtration. Running an assay may include quantification by enzymatic methods, gas chromatography, liquid chromatography, or any combination thereof. The chromatography techniques may use detectors selected from the list consisting of: fluorescence, light absorption, refractive index, mass spectroscopy, and any combination thereof. In some embodiments, microbe fitness level may include more than one fitness property (e.g., fitness level including fitness related to product yield and fitness related to pH tolerance).

The exemplary process flow includes, in step 104, identifying an association between one or more microbe data properties and microbe fitness. In some embodiments, the identified association between one or more data properties of collections of microbes and fitness may be represented by an m by n matrix, wherein m number of data properties are used as input to relate to n fitness properties. In some embodiments, the identified association between one or more data properties and fitness properties may be represented by a function that takes as input m data properties and outputs levels of n fitness properties. In some embodiments, a fitness property may be selected from the list comprising: product yield, microbe productivity, titer, microbe process tolerance, and any combination thereof. In some embodiments, multiple associations may be identified based on the same set of one or more microbe data properties and microbe fitness.

For example, in some embodiments, the association between one or more data properties of collections of microbes and one fitness property may be determined. In a specific example, an association (e.g., model) relating microbe colony size (data property 1) and microbe colony shape (data property 2), as independent variables, to product yield (fitness property), as a dependent variable, may be identified based at least in part on characterization of microbe colony appearance and analysis of microbe fitness. In some embodiments, the identified model may be used to predict the product yield for a microbe colony based on its colony size and colony shape. In some embodiments, the microbe colony size (used, along with microbe colony shape, to predict the product yield based on the identified model) may lie in the range of microbe colony size used to generate the model. In some embodiments, the microbe colony size (used, along with microbe colony shape, to predict the product yield based on the identified model) may lie outside the range of microbe colony size used to generate the model.

In some embodiments, the exemplary process flow includes an optional step, step 105, for selecting collections of microbes based on the identified association between one or more data properties of collections of microbes and microbe fitness. In some embodiments, the identified association and rules related to sample size may be used together to select microbes. For example, the identified association and a requirement to have a number of substantially identical samples may be used to select collections of microbes. In some embodiments, the identified association and rules relating predicted fitness (based on the identified association) to number of required samples may be used to select microbes. For example, more substantially identical samples of collections of microbes predicted to have high levels of productivity and fewer substantially identical samples of collections of microbes predicted to have lower levels of productivity may be selected. In some embodiments where a data property of collections of microbes forms a continuum (as opposed to discrete values), substantially identical samples of collections of microbes may be defined by a range around a given value (as a percentage, for example, +/−10%; as an absolute, for example, +/−0.3 mm² or +/−20 pixels; or using any similar metric) for one or more data properties of collections of microbes. In some embodiments where the data property of collections of microbes forms a continuum (as opposed to discrete values), substantially identical samples of collections of microbes may be defined by using one or more of the mean, median, quartiles, standard deviation or other statistical measures (for example, collections of microbes are substantially identical if a given data property falls in the range of the data property mean+/−data property standard deviation/8) for one or more data properties of collections of microbes. In some embodiments where the data property of collections of microbes takes discrete values, substantially identical samples of collections of microbes may be defined as a set of discrete values. For example, if the data property can be one of six discrete values (A, B, H, K, 2, or 5), substantially identical samples of collections of microbes may be defined as collections of microbes that have a data property equal to A, H, or 5. In some embodiments, collections of microbes, matching the required data properties, may be selected at random from the population of collections of microbes. In some embodiments, the random selection of collections of microbes may be implemented by selecting matching collections of microbes from random locations from one or more source labware.

In some embodiments, exemplary process flow includes an optional step, step 106, for further processing of the selected collections of microbes. In some embodiments, the further processing includes incubation (e.g., growth) of the microbes from the selected collection of microbes. In some embodiments, further processing may include transferring microbes from selected collections of microbes to a destination labware. In some embodiments, further processing may include one or more of adding agar, adding liquid media, adding glass beads, or adding other material to the destination labware before or after transferring the microbes from selected collections of microbes to the destination labware. In some embodiments, further processing may include assay preparation. In some embodiments, exemplary process flow includes an optional step to iterate 107 through one or more of process steps 101, 102, 103, 104, 105 or 106 after further processing of the selected collections of microbes. In some embodiments, one or more process steps may be repeated consecutively or with one or more intervening process steps during the iteration cycle 107 (e.g., following, in order, process steps 101, 102, 101, 102, 103, and 104). In some embodiments, one or more rules to exclude collections of microbes from subsequent processing, e.g., at step 101, 102, 103, 104, 105, or 106, may be implemented during one or more of the identified steps. In some embodiments, one or more rules to include collections of microbes in subsequent processing, for example, as controls, to increase microbe diversity, or to maintain microbe diversity, may be implemented during one or more of the identified steps. In some embodiments, one or more collections of microbes may be selected manually, e.g., by a user, for inclusion in subsequent processing.

Figure 2:
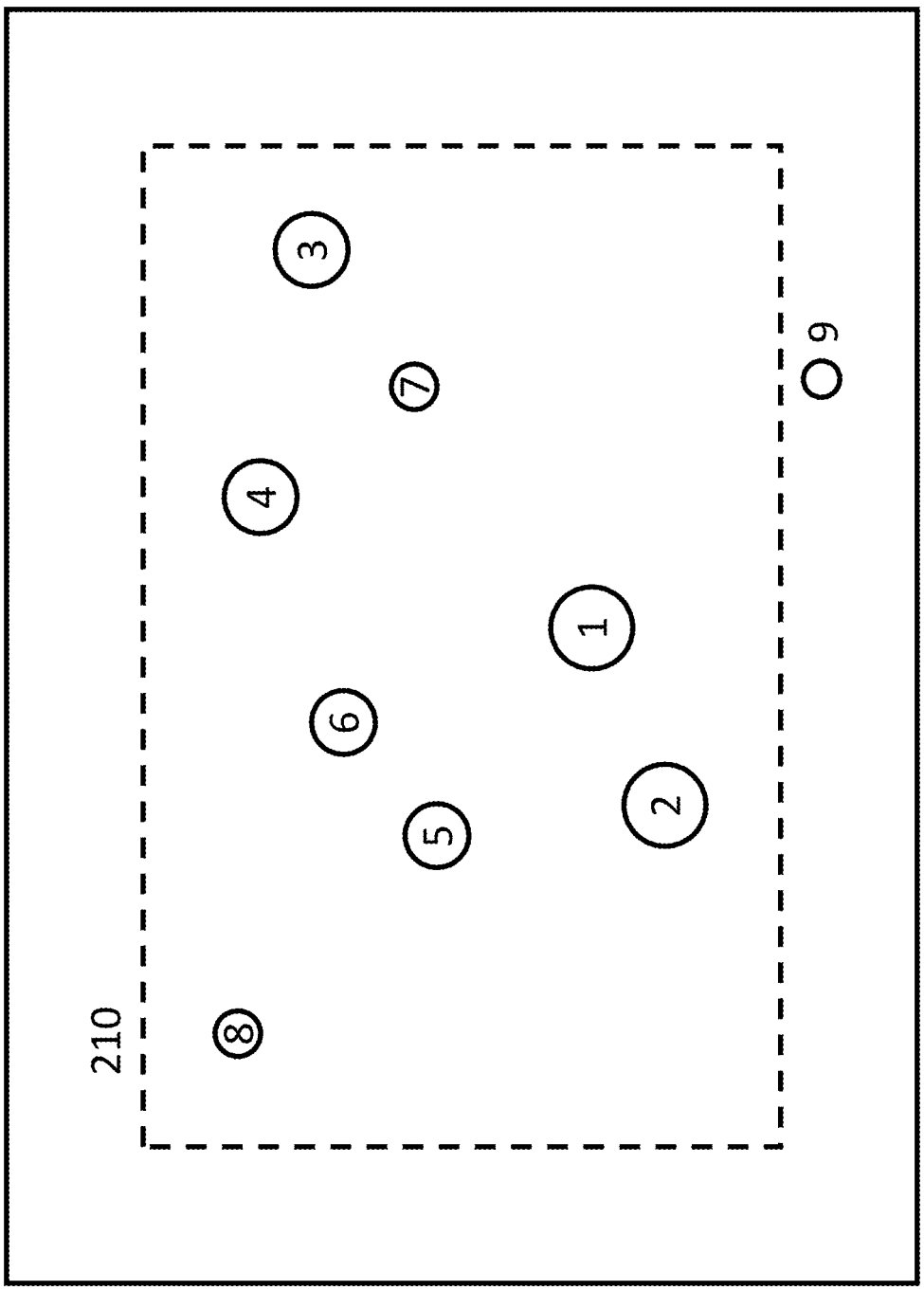
FIG. 2 depicts a schematic image of a source plate including 9 microbe colonies.
Figure 6:
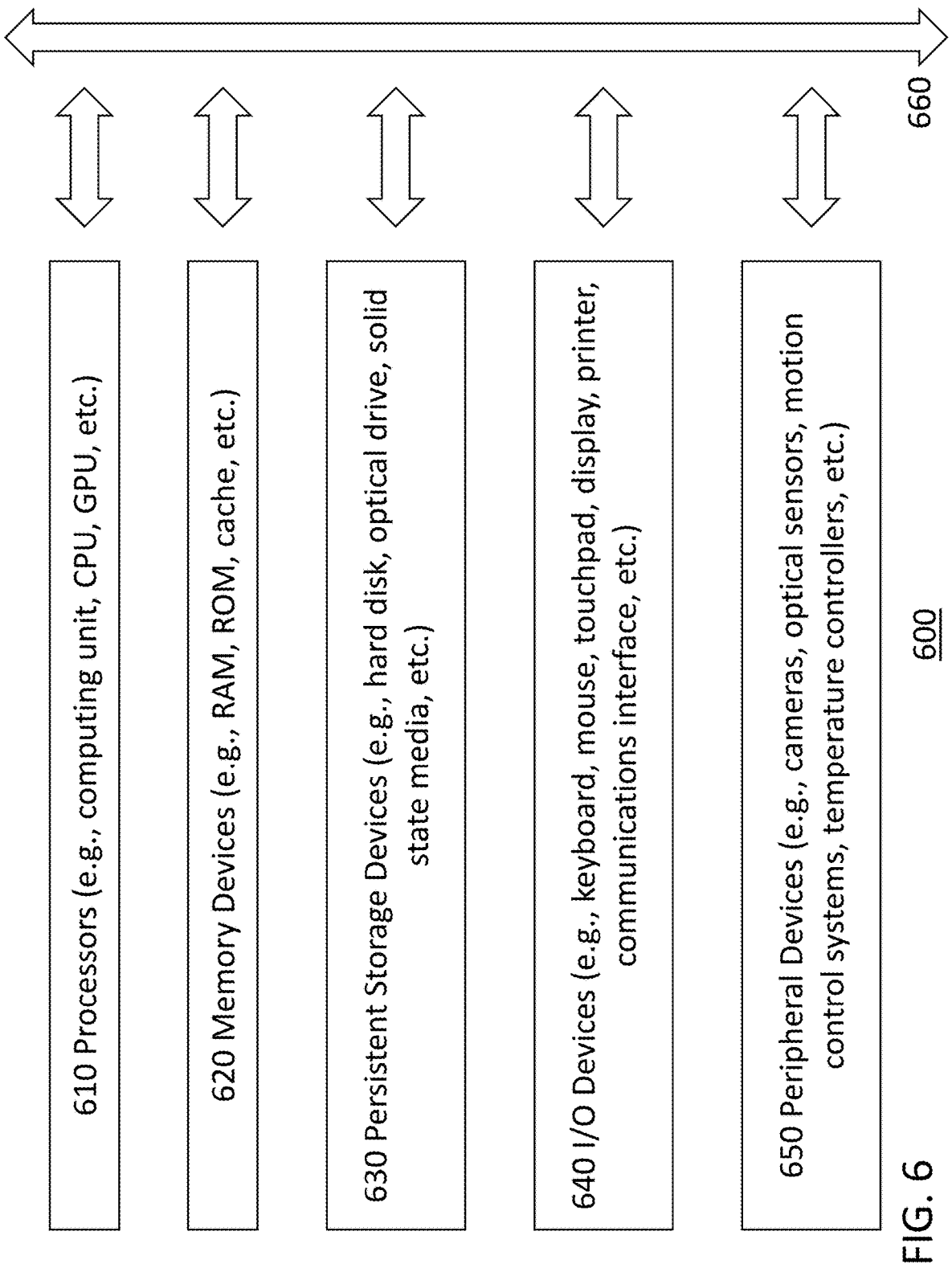
FIG. 6 depicts an exemplary computer system that may be used to implement embodiments of the present disclosure.

FIG. 2 depicts, as a schematic, an exemplary image obtained during the execution of an exemplary process flow based on an embodiment of the disclosure. FIG. 2 shows microbe colonies numbered 1 to 9 on a source plate 211. In some embodiments, an image similar to FIG. 2 may be obtained by imaging microbe colonies on solid agar plates using an automated colony picker. In some embodiments, one or more of the images of collections of microbes may be obtained using top, bottom, or off-axis illumination. In some embodiments, one or more of the images of collections of microbes may include fluorescence data. In some embodiments, one or more of the obtained images may undergo image processing to improve characterization of image properties of collections of microbes (prior to characterization of image properties). The processing of the image to improve characterization of the image properties may include one or more processing techniques selected from the following list: intensity normalization, contrast enhancement, background subtraction, and noise reduction. In some embodiments, image data (e.g., top view image of collections of microbes) may be combined with or processed based on other image data (e.g., dark field image of the same collections of microbes). In some embodiments, image data relating to a reference source plate with agar may be combined with (e.g., subtracted from) the image data relating to the collections of microbes on a test source plate (e.g., without any microbe colonies) with the same or different agar. In some embodiments, the characterization of image properties in an image may be completed by the same computing device, for example, a computer system as shown in FIG. 6, that captures the image. In some embodiments, the characterization of image properties in the image may be completed by a computing device that is different from the computing device that captures the image. In some embodiments, the characterization of data properties of collections of microbes utilizes machine learning algorithms to determine the data properties. Table 1 shows the determined size of microbe colonies 1 to 9 from FIG. 2. In some embodiments, the size may be the microbe colony diameter, microbe colony area, microbe colony length, or microbe colony height. In some embodiments, one or more colony sizes A, B, C, D, or E may represent a size value plus a size range.

TABLE 1

Microbe colony size for colonies shown in FIG. 2.

| Colony No. | Size (e.g., diameter, area, length, height) |
|---|---|
| 1 | A |
| 2 | A |
| 3 | B < A |
| 4 | B < A |
| 5 | C < B |
| 6 | C < B |
| 7 | D < C |
| 8 | D < C |
| 9 | E < D |

Figure 3:
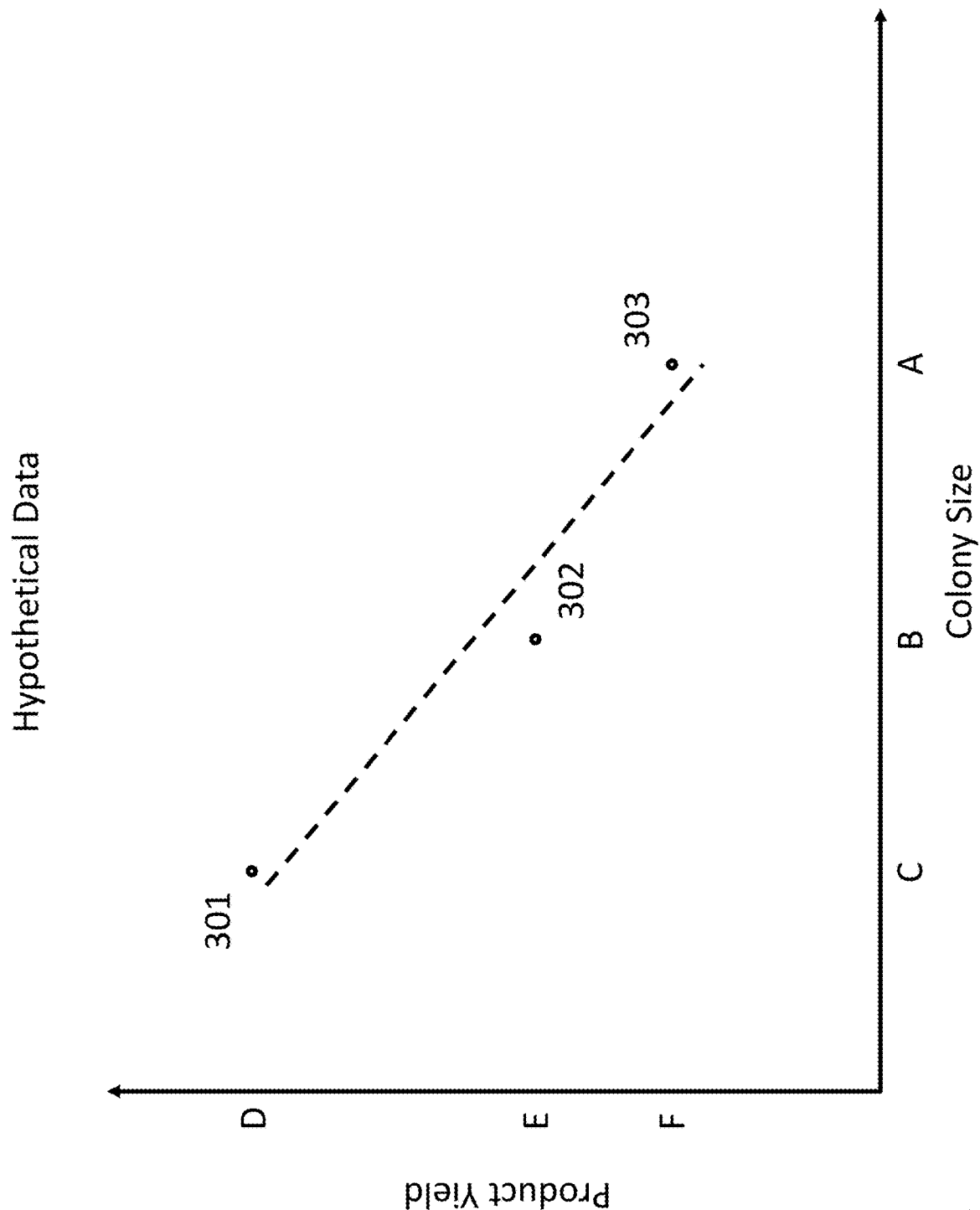
FIG. 3 shows a plot of measured product yield for three microbe colonies from FIG. 2. The dashed line shows a linear fit to the product yield and colony size data. To generate the plot, product yield is measured for each microbe colony, and the product yield for each microbe colony is plotted against the microbe colony's size.

In some embodiments, one or more of the characterized collections of microbes is analyzed for fitness. For example, referring back to FIG. 2 and Table 1, one microbe colony may be selected for analysis from each of 3 determined sizes—A, B, and C. Triplets of microbe colonies that match this criterion include: (1, 3, 5), (1, 3, 6), (1, 4, 5), (1, 4, 6), (2, 3, 5), (2, 3, 6), (2, 4, 5), and (2, 4, 6). Assuming that the triplet of microbe colony numbers (1, 3, 5) is selected for analysis, FIG. 3 shows the results of analyzing microbe colonies 1, 3, and 5 to determine product yield. Specifically, FIG. 3 shows measured product yield (fitness property) versus microbe colony size (microbe image property, dots) and a linear fit (dashed line) for the data. FIG. 3 shows that microbe colony 1 with colony size A produces a measured product yield F (303). Similarly, microbe colony 3 with colony size B produces a measured product yield E (302), and microbe colony 5 with colony size C produces a measured product yield D (301). Based at least in part upon the pairs of colony size and product yield, an association between microbe colony size and product yield is identified. In some embodiments, the association may be characterized as a linearly proportional relationship. In some embodiments, the association may be characterized as the best fit line (e.g., linear fit, dashed line in FIG. 3) for product yield versus colony size data.

In some embodiments, the identified association between the appearance properties of collections of microbes and microbe fitness is used to select collections of microbes for further processing. For example, based on the identified association between the colony size and product yield data from FIG. 3, microbe colonies 7 and 8 may be selected for further processing because they are candidates for higher product yields given the identified association (see, for example, FIG. 3) and because their colony size is D<C. In addition to selecting microbe colonies 7 and 8, microbe colonies 2 and 6 may be selected for further processing to confirm the identified association or to maintain microbe diversity.

In some embodiments, one or more microbes from each of the selected microbe colonies 2, 6, 7, and 8 are picked using an automated colony picker and transferred to individual wells in a well plate filled with liquid media. In some embodiments, the well plate with the picked microbes is placed in an incubator shaker to create a large number of isogenic microbes for each of microbe colonies 2, 6, 7, and 8. In some embodiments, the resulting collection of microbes is then analyzed for fitness (e.g., product yield). Due to non-uniformities of process parameters over the locations of the well array on the well plate, the microbe growth rate or product yield rate may vary from well to well on the same well plate. In some instances, the non-uniformity may be related to differences in well temperature between the wells located near the edge of the well plate and the wells located near the center of the well plate. In some instances, the non-uniformity may be related to differences in well media evaporation rate between the wells located in the well plate. In some instances, the non-uniformity may be related to differences in well light exposure over the wells located in the well plate based on well plate design or equipment design. In some embodiments, non-uniformities may appear in measurement data due to equipment design or data collection processes, e.g., misalignment between well under test and measurement apparatus. In order to account for such non-uniformities when looking for small differences in microbe fitness, in some embodiments, collections of microbes with similar data properties may be randomly distributed over different locations on the destination labware, e.g., to average out the process or measurement non-uniformities.

In the above example, in some embodiments, microbe colonies 7 and 8 may be placed in random well locations in the well plate instead of being placed in adjacent wells in the well plate. In some embodiments, one or more wells in the well plate may be left empty (e.g., not containing any microbes or not containing any media) to, for example, act as control wells. In some embodiments, one or more wells in the well plate may include control microbes to, for example, evaluate: (1) well to well variability within the well plate, (2) well plate to well plate variability during processing or measurement, or (3) experiment to experiment (e.g., run to run, week to week, or batch to batch) variability.

In some embodiments, the locations of the empty wells or the locations of wells with control microbes may be distributed randomly over the array of wells in the well plate. In some embodiments, a single well plate may include wells with collections of microbes from a first source plate and other wells with collections of microbes from a second source plate.

In some embodiments, if new microbe colonies are to be grown from the incubated microbes after incubation, the microbe and media mixture in each well is diluted to yield the microbe density required for additional processing. In some embodiments, the dilution may be adjusted to yield separated individual microbes on a new source agar plate after spotting using a liquid handler, for example, using a Tecan liquid handler. After spotting individual microbes on the new source agar plate, the source agar plate is processed to permit the growth of new microbe colonies from the individual microbes. In some embodiments, the dilution of the media is adjusted based on the target colony size following the growth of microbes, e.g., increased dilution (resulting in larger spacing between individual microbes after spotting) if the colony size is predicted to increase. In some embodiments, the dilution of media is based on OD600. In some embodiments, the dilution is based on colony growth rate or growth time. In some embodiments, the dilution is based on colony size relative to size of other colonies. During processing, the microbe colony source information is tracked to identify the microbe colony number, colony number 2, 6, 7, or 8 in this example, for new microbe colonies grown on the new source agar plate or for analysis of fitness. In some embodiments, images of the new source agar plate are obtained following the additional processing to iterate through the process of identifying a new association between microbe collection image property and microbe fitness or confirming the previously identified association.

In some embodiments, selection rules may dictate when microbe colonies have to be excluded or when microbe colonies have to be included in the subsequent process steps. In one embodiment, a selection rule may exclude colonies that are too close to the edge of source plate, e.g., source plate 211 in FIG. 2. In one embodiment, a source plate exclusion zone may be implemented such that colonies that lie outside of a predefined zone, for example, outside dashed line 210 in FIG. 2, may not be used in subsequent process steps. Using this rule, microbe colony 9 may not be selected for further processing because it lies outside the region defined by dashed line 210. Microbe colony 9 may not be selected even though it is the smallest colony and, based on the identified association, likely to have the highest product yield.

In some embodiments, an association relating one or more data properties to fitness may be used to predict the fitness level of one or more collections of microbes. In an exemplary embodiment, data relating to a collection of microbes is obtained. One or more data properties of the collection of microbes is determined based at least in part upon the obtained data. A predicted fitness level for the collection of microbes is determined based at least in part upon the association relating the determined one or more data properties and the fitness level. For example, the association identified based on data from microbe colonies 1, 3, and 5 from FIG. 2 may be used to identify the predicted product yield (fitness) of the other microbe colonies based on their colony size.

In some embodiments, data relating to each collection of microbes from a plurality of collections microbes may be obtained for microbe collection appearance characterization. In an exemplary process flow, optical data is obtained for each collection of microbes in a plurality of collections of microbes. The optical data is analyzed to characterize the appearance of each collection of microbe. In this example with 8 groups of microbes, the optical data is fluorescence data, and the analysis of the optical data identifies the fluorescence intensity for each group of microbes. Each of the 8 groups of microbes has a fluorescence intensity selected from about G, about H, or about I. In this exemplary process flow, analyzing the optically characterized groups of microbes to determine productivity shows that the 8 groups of microbes have a productivity of about J, a productivity of about K, or a productivity of about L.

Figure 8:
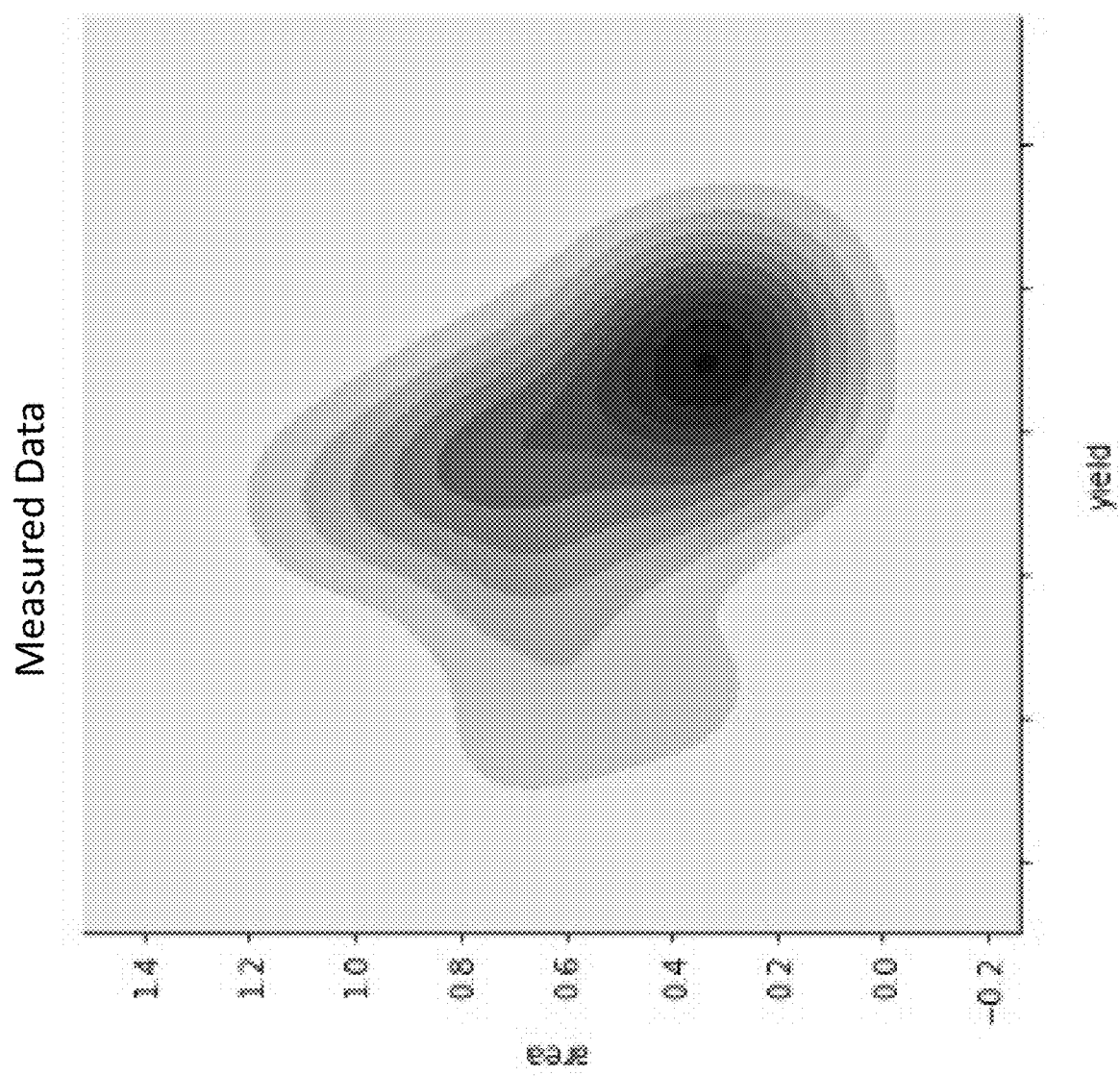
FIG. 8 shows an intensity plot of measured yield for a collection of microbe colonies.

FIG. 8 shows a plot of measured colony area (e.g., 0, 0.2, . . . , 1.2, 1.4 mm$^2$) versus measured yield of a biomolecule for a plurality of bacterial colonies. The colony area is shown plotted along the y-axis. The yield of the biomolecule is plotted along the x-axis. The colony area versus yield data is shown as an intensity plot with the darker intensity corresponding to a higher density of individual-colony data points (e.g., pairs of colony area and yield; most colonies having an area of approximately 0.4). The identified association between colony area and yield mirrors the hypothetical product yield and colony size shown in FIG. 3, with smaller colony area in FIG. 8 (smaller colony size in FIG. 3) corresponding to larger yield in FIG. 8 (larger product yield in FIG. 3).

Figure 9:
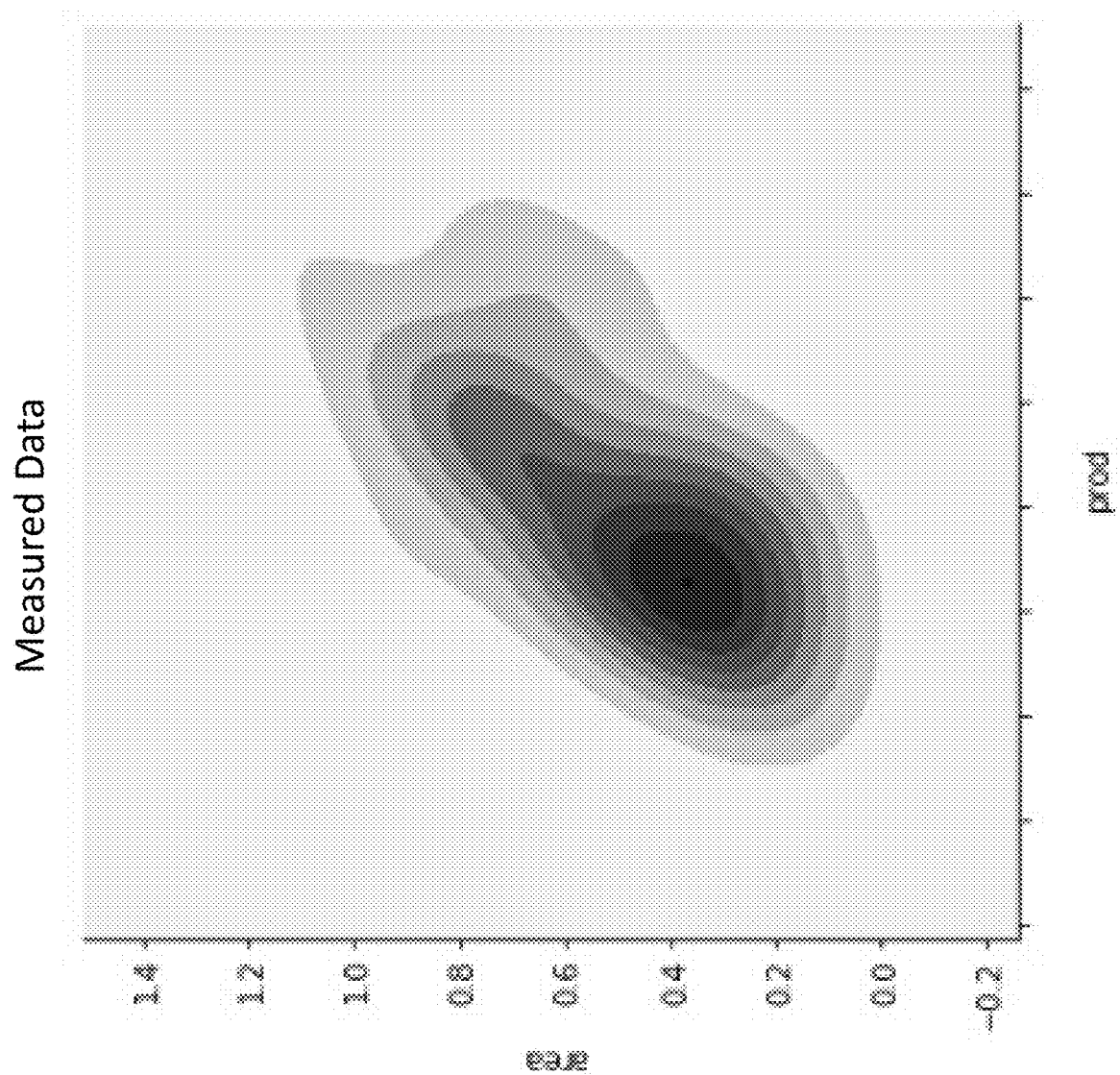
FIG. 9 shows an intensity plot of measured productivity for a collection of microbe colonies.

FIG. 9 shows a plot of measured colony area (e.g., 0, 0.2, . . . , 1.2, 1.4 mm$^2$) versus measured productivity of a biomolecule for a plurality of bacterial colonies. The colony area is plotted along the y-axis. The productivity is plotted along the x-axis. The colony area versus productivity data is shown as an intensity plot with the darker intensity corresponding to a higher density of individual-colony data points (e.g., pairs of colony area and productivity; most colonies having an area of approximately 0.4). The identified association between colony area and productivity may be used to predict that colonies of larger area would correspond to higher productivity.

Figure 4:
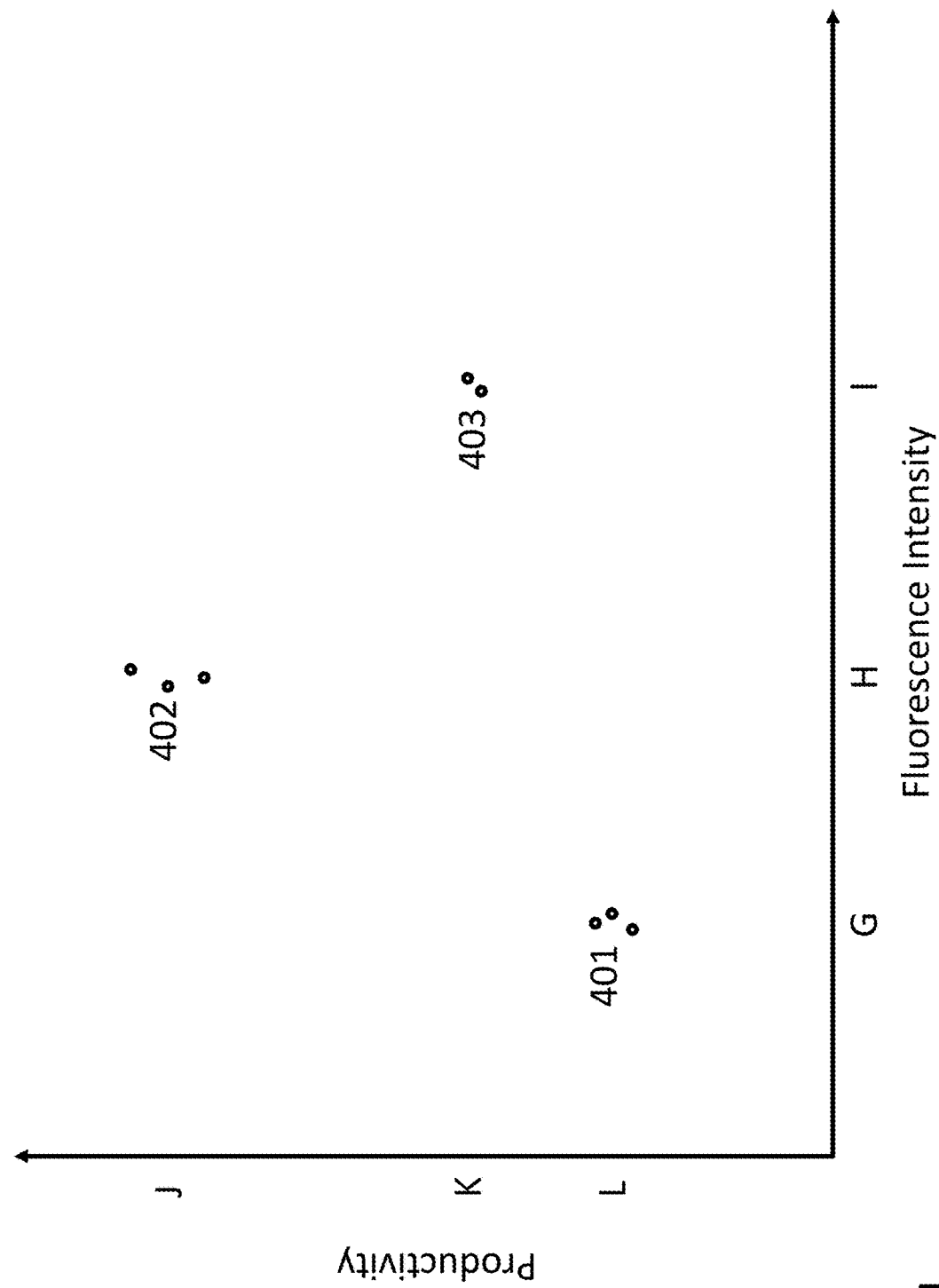
FIG. 4 shows a plot of measured productivity for 8 groups of microbes. To generate the plot, the fluorescence intensity, of a marker attached to microbes in the group, is determined for each group of microbes. The productivity is measured for each group of microbes, and the productivity for each group of microbes is plotted against the group's fluorescence intensity.

FIG. 4 shows a plot of 8 data points (one for each group of microbes) showing the group's measured productivity versus measured fluorescence intensity (e.g., biology specific relative fluorescence unit). FIG. 4 shows that the data for the 8 groups of microbes clusters into three distinct data groups, labeled 401, 402, and 403. In this exemplary process flow, based at least in part upon the measured fluorescence intensity and measured productivity, an association between the fluorescence intensity and productivity is identified—groups of microbes with fluorescence intensity equal to about H are likely to yield higher productivity. In an optional step in this exemplary process flow, groups of microbes with fluorescence intensity equal to about H are selected for further processing. In addition to selecting groups of microbes with fluorescence intensity equal to about H, groups of microbes with fluorescence intensity equal to about G and about I may also be selected for further processing (e.g., as controls to evaluate the identified association). In some embodiments, the selected number of groups of microbes with fluorescence intensity equal to about H may be larger than the selected number of groups of microbes with fluorescence intensity equal to about G or about I. Given group to group variability or process variability in measuring productivity (fitness), using statistical analysis, the increased number of groups of microbes with fluorescence intensity equal to about H permits a more accurate estimate of the productivity for groups of microbes with fluorescence intensity equal to about H. In some embodiments, the assignment of groups of microbes into clusters with fluorescence intensity equal to about H, about G, and about I may be defined by binning the fluorescence intensity for each group of microbes into a cluster based on a range for the fluorescence intensity. In some embodiments, the assignment of groups of microbes into clusters with fluorescence intensity equal to about H, about G, and about I may be defined by binning the fluorescence intensity for each group of microbes into a cluster based on a target fluorescence intensity plus or minus a fluorescence intensity variation about the target fluorescence intensity.

Figure 5:
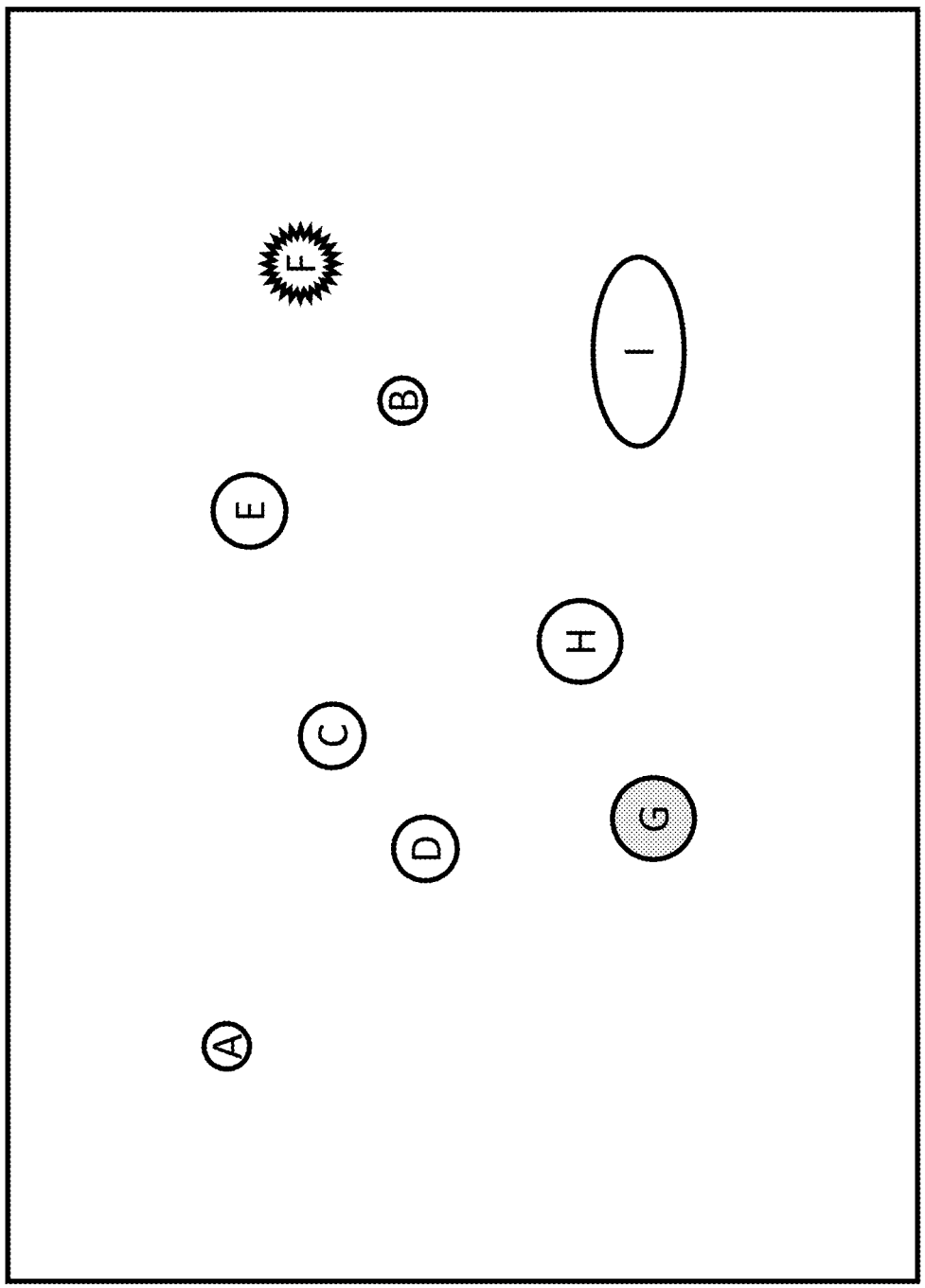
FIG. 5 depicts a schematic image of a source plate including 9 microbe colonies having different types of image properties.

FIG. 5 depicts, as a schematic, an exemplary image obtained during the execution of an exemplary process flow based on an embodiment of the disclosure. FIG. 5 shows microbe colonies labeled A to I on a source plate 511. Ignoring differences in colony size, microbe colonies F, G, and I have image properties that are different from the image properties associated with the remaining colonies. Specifically, microbe colony F has edge roughness. Microbe colony G has a different opacity. And, microbe colony I has a different eccentricity. In some embodiments, data from characterizing the microbe appearance may be used to filter out microbes from further processing. For example, microbe colonies F, G, and I may be excluded from analysis for fitness because they differ in appearance. In some embodiments, microbe colonies F, G, and I may be included in the analysis for fitness with the difference in appearance appearing as a factor in the identified association.

In some embodiments, values of one or more data properties of a collection of microbes may be used along with an association relating one or more data properties to contaminating microbes to identify that the collection of microbes includes contaminating microbes. For example, an association may indicate that microbe colonies including contaminating microbes have rough edges. In this example, based on the association, it may be inferred that a microbe colony having rough edges, determined based on image data, includes contaminating microbes. Colonies identified as having contaminating microbes may be excluded from selection for further processing. In some embodiments, collections of microbes including contaminating microbes may be determined based on one or more image properties related to the following one or more properties of at least one corresponding collections of microbes: size, color, shape, eccentricity, aspect ratio, opacity, contrast, edge roughness, edge sharpness, uniformity, intensity, intensity profile, opacity profile, uniformity profile, number of concavities, or any combination thereof. In some embodiments, the shape image property may be related to one or more of microbe collection eccentricity, aspect ratio, edge roughness, topology, number of concavities, or the like. In some embodiments, the image property may be related to contrast (e.g., brightness relative to background) of a collection of microbes. In some embodiments, an association may relate one or more data properties to differences between collections of microbes of interest and collections of microbes including contaminating microbes. In some embodiments, the contaminating microbes may be the same species as the microbes in the collections of microbes of interest. In some embodiments, the contaminating microbes may a different species compared to the species of microbes in the collections of microbes of interest.

In some embodiments, data describing one or more associations may be stored in one or more data structures (collectively referred to herein as a "library" for the sake of convenience). A library may include annotations related to one or more associations. The annotations may include one or more of: information identifying the collections of microbes that relate to an association (e.g., microbe species), information identifying one or more process conditions that relate to an association (e.g., pH level, temperature, time), information identifying one or more data properties that relate to an association (e.g., fluorescence intensity, size of a collection of microbes, colony diameter, colony shape), or information identifying one or more fitness properties that relate to an association (e.g., productivity, titer). In some embodiments, a client computer system may access data in the library using a software as a service (SaaS) platform. The client computer system may access the data in the library by connecting to a cloud computing system hosting the library, a computer system hosting the library, or the like. In some embodiments, the client computer system may search for associations related to a particular species of microbes. In some embodiments, the client computer may search for associations related to a given set of process parameters. In some embodiments, the client computer may search for associations using one or more annotations. In some embodiments, the client computer may search for annotations related to one or more associations. In some embodiments, the client computer may add annotations to the library. In some embodiments, the client computer may update associations, update annotations related to one or more associations, or add new associations in the library.

A software as a service (SaaS) platform may perform a process in accordance with an embodiment of the present disclosure. In some embodiments, a SaaS platform may obtain data relating to a plurality of collections of microbes (e.g., from a client computer). In some embodiments, a SaaS platform may determine one or more data properties of each of the collections of microbes in a first set of the plurality of collections of microbes based at least in part upon the data. In some embodiments, a SaaS platform may determine an expressed fitness of each of the collections of microbes in the first set (e.g., receiving data related to the expressed fitness from a client computer). In some embodiments, a SaaS platform may identify an association between the determined one or more data properties and expressed fitness levels of one or more collections of microbes in the first set. A single SaaS platform may perform one or more of these acts.

In some embodiments, a SaaS platform may obtain data relating to a collection of microbes (e.g., from a client computer). In some embodiments, a SaaS platform may determine one or more data properties of the collection of microbes based at least in part upon the data. In some embodiments, a SaaS platform may determine a predicted fitness level for the collection of microbes based at least in part upon an association (e.g., received from: a client computer, from a library on the SaaS platform, or from another SaaS platform containing the library) relating the determined one or more data properties and the fitness.

A SaaS platform may be a part of a system in accordance with an embodiment of the present disclosure. A SaaS platform may include one or more non-transitory computer readable media in accordance with an embodiment of the present disclosure.

FIG. 6 shows an example of a computer system 600 that may be used to execute program code stored in one or more non-transitory computer readable media (e.g., memory) in accordance with embodiments of the present disclosure. The computer system includes an input/output (I/O) subsystem, with I/O devices 640, which may be used to implement an input interface to interface with human users and/or other computer systems depending upon the application. For example, some embodiments of the present disclosure may be may be implemented in program code on system 600 with I/O subsystem used to receive input commands from a human user (e.g., via a GUI or keyboard) and to display data or results back to the user. The I/O subsystem may include, e.g., a keyboard, mouse, graphical user interface, touchscreen, or other interfaces for input, and, e.g., an LED or other flat screen display, or other interfaces for output. In some embodiments, program code stored in a non-transitory computer readable medium may, when executed on one or more processors, provide application programming interfaces (APIs). Other elements of embodiments of the present disclosure may be implemented with a computer system like that of computer system 600, perhaps, however, without I/O.

Program code may be stored in non-transitory media such as memory devices 620 or persistent storage devices 630 or both. Memory devices 620 may include volatile memory such as random access memory (RAM) or non-volatile memory such as read only memory (ROM), as well as different levels of cache memory for faster access to instructions and data. Persistent storage devices 630 may include solid state devices (SSD), hard disk drives, hybrid hard disk drives (with integrated SSD), or optical disks. In some embodiments, computer system 600 may use one or more devices as both memory devices and persistent storage devices. One or more processors 610 read program code from one or more non-transitory media and execute the code to enable the computer system to accomplish the methods performed by the embodiments disclosed herein, for example, such as those represented by the flow chart of FIG. 1. Processor(s) 610 may include one or more graphics processing units (GPUs) for handing computationally intensive tasks. Those skilled in the art will understand that a processor may ingest source code and interpret or compile the source code into machine code that is understandable at the hardware gate level of the processor. One or more buses 660 couple one or more processors 610, one or more memory devices 620, one or more persistent storage devices 630, one or more of the I/O devices 640, or one or more peripheral devices 650 to one or more components in computer system 600.

The processor(s) 610 may communicate with external networks via one or more communications interfaces, e.g., network interface card, Wi-Fi transceiver, cellular modem, etc., in the I/O subsystem. Computer system 600 may include peripheral devices 650, e.g., cameras, optical sensors, motion control system, temperature controllers, etc.

Those skilled in the art will understand that some or all of the elements of disclosed embodiments may be implemented wholly or partially on one or more computer systems including one or more processors and one or more memory systems like those of computer system 600. Some elements and functionality may be implemented locally and others may be implemented in a distributed fashion over a network through different computer systems, e.g. servers, e.g., in client-server fashion, for example. In some embodiments, server-side operations may be made available to multiple clients in a software as a service (SaaS) fashion.

The term component in this context refers broadly to software, hardware (e.g., device), or firmware (or any combination thereof) component. Components are typically functional components that can generate useful data or other output using specified input(s). A component may or may not be self-contained. An application program (also called an "application") may include one or more components, or a component can include one or more application programs.

Some embodiments include some, all, or none of the components along with other modules or application components. Still yet, various embodiments may incorporate two or more of these components into a single module and/or associate a portion of the functionality of one or more of these components with a different component.

The term "memory" can be any device or mechanism used for storing information. In accordance with some embodiments of the present disclosure, memory is intended to encompass any type of, but is not limited to: volatile memory, nonvolatile memory, and dynamic memory. For example, memory can be random access memory, memory storage devices, optical memory devices, magnetic media, floppy disks, magnetic tapes, hard drives, SIMMs, SDRAM, DIMMs, RDRAM, DDR RAM, SODIMMS, erasable programmable read-only memories (EPROMs), electrically erasable programmable read-only memories (EEPROMs), compact disks, DVDs, and/or the like. In accordance with some embodiments, memory may include one or more disk drives, flash drives, databases, local cache memories, processor cache memories, relational databases, flat databases, servers, cloud based platforms, and/or the like. In addition, those of ordinary skill in the art will appreciate many additional devices and techniques for storing information can be used as memory.

Memory may be used to store instructions for running one or more applications or modules on one or more processors. For example, memory could be used in some embodiments to house all or some of the instructions needed to execute the functionality of one or more of the modules and/or applications disclosed in this application.

Figure 7:
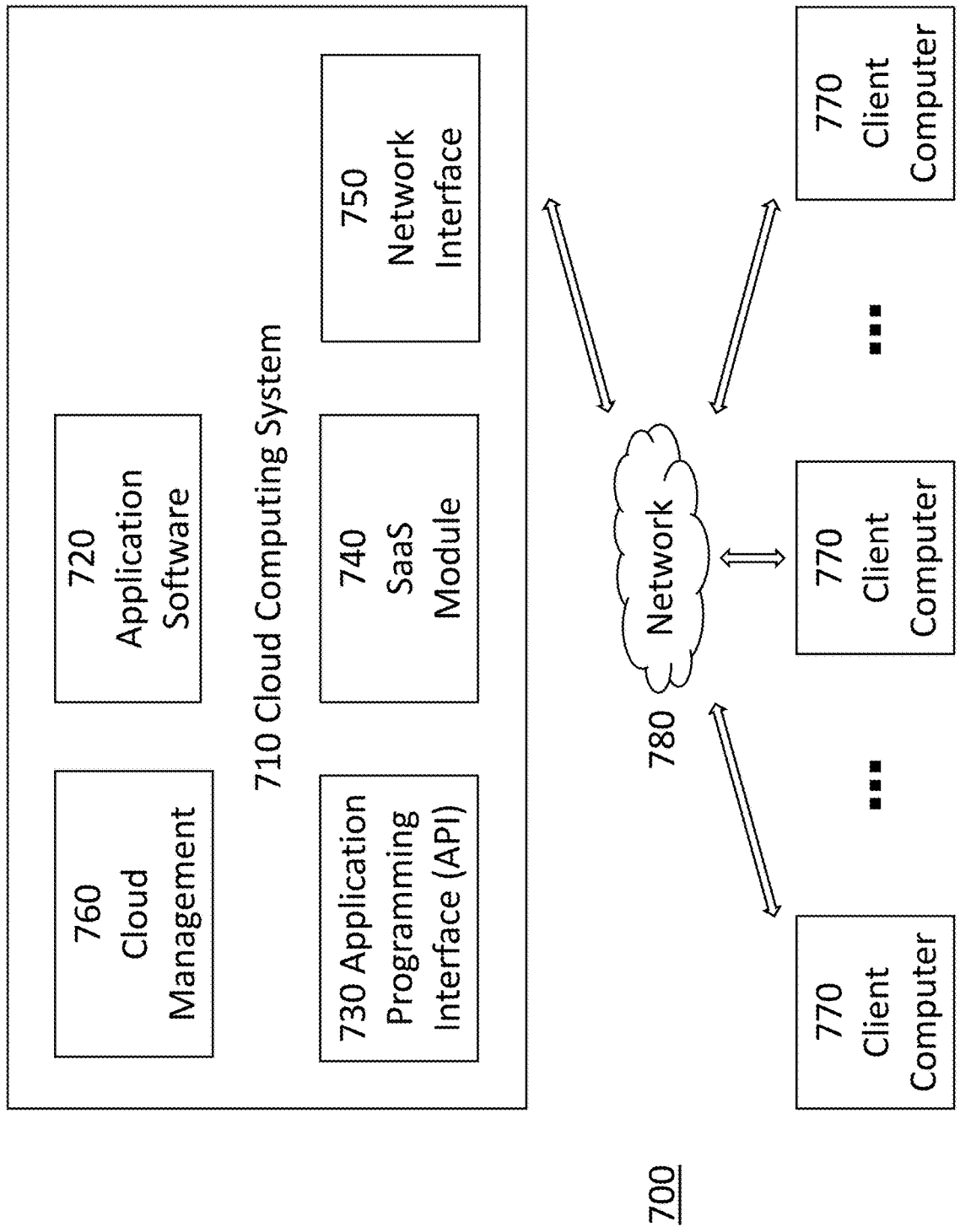
FIG. 7 depicts an exemplary cloud computing environment that may be used to implement embodiment of the present disclosure.

FIG. 7 shows an example of a cloud computing environment 700 implementing an embodiment of the present disclosure. One or more client computers 770, of the type illustrated in FIG. 6, access the cloud computing system 710 via a network 780, e.g., the Internet. In some embodiments, application software 720 resides in the cloud computing system 710. The cloud computing system may employ one or more computer systems, of the type illustrated in FIG. 6. The cloud computing system 710 may include a network interface 750 to interface application software 720 to the client computers 770 via the network 780. The cloud computing system 710 may include an application programming interface (API) 730 to enable client applications at the client computers 770 to access the application software 720. In some embodiments, through the API 730, client computers 770 may access an association library via the application software 720. In some embodiments, a software as a service (SaaS) software module 740 offers the application software 720 as a service to client computers 770. In some embodiments, a cloud management module 760 manages access to the cloud computing system 710 by the client computers 770. The cloud management module 760 may enable a cloud architecture that employs multitenant applications, virtualization, or other architectures known in the art to serve multiple client computers 770.

As used herein, "based at least in part upon A and B" means "based at least in part upon A and based at least in part upon B."

While the present disclosure has been particularly described with respect to the illustrated embodiments, it will be appreciated that various alterations, modifications and adaptations may be made based on the present disclosure, and are intended to be within the scope of the present disclosure. While the disclosure has been described in connection with the disclosed embodiments, it is to be understood that the present disclosure is not limited to the disclosed embodiments but, on the contrary, is intended to cover various modifications and equivalent arrangements included within the scope of the claims.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

Embodiments

1. A computer-implemented method of identifying a collection of microbes with variable fitness, the method comprising:
   a. obtaining, by a computing device, data relating to a plurality of collections of microbes, wherein one or more of the collections of microbes have a different fitness level than at least one of the other collections of microbes,
      i. wherein the data is related to appearance of the plurality of collections of microbes;
   b. determining, by a computing device, one or more data properties of each of the collection of microbes in a first set of the plurality of collections of microbes based at least in part upon the data;
   c. determining an expressed fitness level of each of the collection of microbes in the first set; and
   d. identifying an association between the determined one or more data properties and expressed fitness level of one or more of the collections of microbes in the first set,
      i. wherein selection of a candidate collection of microbes is based at least in part upon application of the identified association and the candidate collection of microbes having one or more desired data properties.
2. The method of embodiment 1, wherein each collection of microbes includes only one microbe.
3. The method of embodiment 1, wherein each collection of microbes is a group of two or more microbes.
4. The method of embodiment 3, wherein each group contains less than or equal to 100 microbes.
5. The method of embodiment 1, wherein each collection of microbes is a microbe colony.
6. The method of embodiment 5, wherein each microbe colony contains more than 100 microbes.
7. The method of any one of embodiments 1-6, wherein microbes in each of the collections of microbes are from the same species.
8. The method of any one of embodiments 1-7, wherein microbes in each of the collections of microbes are isogenic.
9. The method of any one of embodiments 1-8, wherein microbes in the plurality of collections of microbes are from the same species.
10. The method of any one of embodiments 1-9, wherein the possible values of a data property are discrete.
11. The method of any one of embodiments 1-10, wherein the possible values of a data property are selected from a continuous range.

12. The method of any one of embodiments 1-11, wherein the data is image data and the one or more data properties are one or more image properties.
13. The method of embodiment 12, wherein the one or more image properties are: size, color, eccentricity, aspect ratio, opacity, edge roughness, edge sharpness, fluorescence, uniformity, topology, height, opacity profile, uniformity profile, fluorescence profile, height profile, distance to a nearest neighboring collection of microbes, growth rate, local density of the collections of microbes, or any combination thereof, wherein the local density of a collection of microbes is based at least in part upon one or more of: a predetermined radius about each collection of microbes, a size of each collection of microbes, or a predetermined number of collections of microbes surrounding each collection of microbes.
14. The method of any one of embodiments 1-13, further comprising:
    a. selecting one or more candidate collections of microbes based at least in part upon application of the identified association and each of the candidate collections of microbes having the one or more desired data properties.
15. The method of embodiment 14, wherein the selected one or more desired collections of microbes are candidates with improved fitness relative to at least one collection of microbes in the plurality of collections of microbes.
16. The method of embodiment 14, wherein the selected one or more desired collections of microbes are candidates with reduced fitness relative to at least one collection of microbes in the plurality of collections of microbes.
17. The method of any one of embodiments 14-16, further comprising:
    a. obtaining, by a computing device, second data relating to one or more selected collections of microbes,
        i. wherein the second data is related to appearance of the one or more selected collections of microbes.
18. The method of any one of embodiments 14-17, further comprising:
    a. determining, by a computing device, one or more data properties of each collection of microbes in a second set of collections of microbes based at least in part upon obtained data relating to each collection of microbes.
19. The method of any one of embodiments 14-18, further comprising:
    a. determining an expressed fitness level of each collection of microbes in a third set of collections of microbes.
20. The method of any one of embodiments 14-16, further comprising:
    a. obtaining, by a computing device, second data relating to a second set of the one or more selected collections of microbes,
        i. wherein the second data is related to appearance of the second set of collections of microbes;
    b. determining, by a computing device, one or more data properties of each of the collection of microbes in a third set of collections of microbes based at least in part upon the second data, wherein each collection of microbes in the third set is also in the second set;
    c. determining an expressed fitness level of each of the collections of microbes in the third set; and
    d. identifying a second association between the determined one or more data properties and expressed fitness level of one or more of the collections of microbes in the third set.
21. The method of any one of embodiments 1-20, wherein the one or more desired data properties are based at least in part upon application of the identified association to a desired fitness level.
22. A system for identifying a collection of microbes with variable fitness, the system comprising:
    a. one or more processors; and
    b. one or more memories operatively coupled to at least one of the one or more processors and having instructions stored thereon that, when executed by at least one of the one or more processors, cause the system to:
        i. obtain data relating to a plurality of collections of microbes, wherein one or more of the collections of microbes have a different fitness level than at least one of the other collections of microbes,
            1. wherein the data is related to appearance of the plurality of collections of microbes;
        ii. determine one or more data properties of each of the collection of microbes in a first set of the plurality of collections of microbes based at least in part upon the data;
        iii. determine an expressed fitness level of each of the collection of microbes in the first set; and
        iv. identify an association between the determined one or more data properties and expressed fitness level of one or more of the collections of microbes in the first set,
            1. wherein selection of a candidate collection of microbes is based at least in part upon application of the identified association and the candidate collection of microbes having one or more desired data properties.
23. The system of embodiment 22, wherein each collection of microbes includes only one microbe.
24. The system of embodiment 22, wherein each collection of microbes is a group of two or more microbes.
25. The system of embodiment 24, wherein each group contains less than or equal to 100 microbes.
26. The system of embodiment 22, wherein each collection of microbes is a microbe colony.
27. The system of embodiment 26, wherein each microbe colony contains more than 100 microbes.
28. The system of any one of embodiments 22-27, wherein microbes in each of the collections of microbes are from the same species.
29. The system of any one of embodiments 22-28, wherein microbes in each of the collections of microbes are isogenic.
30. The system of any one of embodiments 22-29, wherein microbes in the plurality of collections of microbes are from the same species.
31. The system of any one of embodiments 22-30, wherein the possible values of a data property are discrete.
32. The system of any one of embodiments 22-31, wherein the possible values of a data property are selected from a continuous range.
33. The system of any one of embodiments 22-32, wherein the data is image data and the one or more data properties are one or more image properties.
34. The system of embodiment 33, wherein the one or more image properties are: size, color, eccentricity, aspect ratio, opacity, edge roughness, edge sharpness, fluorescence, uniformity, topology, height, opacity profile, uniformity profile, fluorescence profile, height profile, distance to a nearest neighboring collection of microbes, growth rate, local density of the collections of microbes, or any combination thereof, wherein the local density of a collection of microbes is based at least in part upon one or more of: a predetermined radius about each collection of microbes, a size of each collection of microbes, or a predetermined number of collections of microbes surrounding each collection of microbes.

35. The system of any one of embodiments 22-34, wherein at least one of the one or more memories operatively coupled to at least one of the one or more processors has instructions stored thereon that, when executed by at least one of the one or more processors, cause the system to:
    a. select one or more candidate collections of microbes based at least in part upon application of the identified association and each of the candidate collections of microbes having the one or more desired data properties.

36. The system of embodiment 35, wherein the selected one or more desired collections of microbes are candidates with improved fitness relative to at least one collection of microbes in the plurality of collections of microbes.

37. The system of embodiment 35, wherein the selected one or more desired collections of microbes are candidates with reduced fitness relative to at least one collection of microbes in the plurality of collections of microbes.

38. The system of any one of embodiments 35-37, wherein at least one of the one or more memories operatively coupled to at least one of the one or more processors has instructions stored thereon that, when executed by at least one of the one or more processors, cause the system to:
    a. obtain second data relating to one or more selected collections of microbes,
        i. wherein the second data is related to appearance of the one or more selected collections of microbes.

39. The system of any one of embodiments 35-38, wherein at least one of the one or more memories operatively coupled to at least one of the one or more processors has instructions stored thereon that, when executed by at least one of the one or more processors, cause the system to:
    a. determine one or more data properties of each collection of microbes in a second set of collections of microbes based at least in part upon obtained data relating to each collection of microbes.

40. The system of any one of embodiments 35-39, wherein at least one of the one or more memories operatively coupled to at least one of the one or more processors has instructions stored thereon that, when executed by at least one of the one or more processors, cause the system to:
    a. determine an expressed fitness level of each collection of microbes in a third set of collections of microbes.

41. The system of any one of embodiments 35-37, wherein at least one of the one or more memories operatively coupled to at least one of the one or more processors has instructions stored thereon that, when executed by at least one of the one or more processors, cause the system to:
    a. obtain second data relating to a second set of the one or more selected collections of microbes,
        i. wherein the second data is related to appearance of the second set of collections of microbes;
    b. determine one or more data properties of each of the collection of microbes in a third set of collections of microbes based at least in part upon the second data, wherein each collection of microbes in the third set is also in the second set;
    c. determine an expressed fitness level of each of the collections of microbes in the third set; and
    d. identify a second association between the determined one or more data properties and expressed fitness level of one or more of the collections of microbes in the third set.

42. The system of any one of embodiments 22-41, wherein the one or more desired data properties are based at least in part upon application of the identified association to a desired fitness level.

43. One or more computer readable media storing instructions for identifying a collection of microbes with variable fitness, wherein the instructions, when executed by one or more computing devices, cause at least one of the one or more computing devices to:
    a. obtain data relating to a plurality of collections of microbes, wherein one or more of the collections of microbes have a different fitness level than at least one of the other collections of microbes,
        i. wherein the data is related to appearance of the plurality of collections of microbes;
    b. determine one or more data properties of each of the collection of microbes in a first set of the plurality of collections of microbes based at least in part upon the data;
    c. determine an expressed fitness level of each of the collection of microbes in the first set; and
    d. identify an association between the determined one or more data properties and expressed fitness level of one or more of the collections of microbes in the first set,
        i. wherein selection of a candidate collection of microbes is based at least in part upon application of the identified association and the candidate collection of microbes having one or more desired data properties.

44. The computer readable media of embodiment 43, wherein each collection of microbes includes only one microbe.

45. The computer readable media of embodiment 43, wherein each collection of microbes is a group of two or more microbes.

46. The computer readable media of embodiment 45, wherein each group contains less than or equal to 100 microbes.

47. The computer readable media of embodiment 43, wherein each collection of microbes is a microbe colony.

48. The computer readable media of embodiment 47, wherein each microbe colony contains more than 100 microbes.

49. The computer readable media of any one of embodiments 43-48, wherein microbes in each of the collections of microbes are from the same species.

50. The computer readable media of any one of embodiments 43-49, wherein microbes in each of the collections of microbes are isogenic.
51. The computer readable media of any one of embodiments 43-50, wherein microbes in the plurality of collections of microbes are from the same species.
52. The computer readable media of any one of cla embodiments ims 43-51, wherein the possible values of a data property are discrete.
53. The computer readable media of any one of embodiments 43-52, wherein the possible values of a data property are selected from a continuous range.
54. The computer readable media of any one of embodiments 43-53, wherein the data is image data and the one or more data properties are one or more image properties.
55. The computer readable media of embodiment 54, wherein the one or more image properties are: size, color, eccentricity, aspect ratio, opacity, edge roughness, edge sharpness, fluorescence, uniformity, topology, height, opacity profile, uniformity profile, fluorescence profile, height profile, distance to a nearest neighboring collection of microbes, growth rate, local density of the collections of microbes, or any combination thereof, wherein the local density of a collection of microbes is based at least in part upon one or more of: a predetermined radius about each collection of microbes, a size of each collection of microbes, or a predetermined number of collections of microbes surrounding each collection of microbes.
56. The computer readable media of any one of embodiments 43-55, storing instructions that, when executed by the one or more computing devices, cause at least one of the one or more computing devices to:
    a. select one or more candidate collections of microbes based at least in part upon application of the identified association and each of the candidate collections of microbes having the one or more desired data properties.
57. The computer readable media of embodiment 56, wherein the selected one or more desired collections of microbes are candidates with improved fitness relative to at least one collection of microbes in the plurality of collections of microbes.
58. The computer readable media of embodiment 56, wherein the selected one or more desired collections of microbes are candidates with reduced fitness relative to at least one collection of microbes in the plurality of collections of microbes.
59. The computer readable media of any one of embodiments 56-58, storing instructions that, when executed by the one or more computing devices, cause at least one of the one or more computing devices to:
    a. obtain second data relating to one or more selected collections of microbes,
        i. wherein the second data is related to appearance of the one or more selected collections of microbes.
60. The computer readable media of any one of embodiments 56-59, storing instructions that, when executed by the one or more computing devices, cause at least one of the one or more computing devices to:
    a. determine one or more data properties of each collection of microbes in a second set of collections of microbes based at least in part upon obtained data relating to each collection of microbes.
61. The computer readable media of any one of embodiments 56-60, storing instructions that, when executed by the one or more computing devices, cause at least one of the one or more computing devices to:
    a. determine an expressed fitness level of each collection of microbes in a third set of collections of microbes.
62. The computer readable media of any one of embodiments 56-58, storing instructions that, when executed by the one or more computing devices, cause at least one of the one or more computing devices to:
    a. obtain second data relating to a second set of the one or more selected collections of microbes,
        i. wherein the second data is related to appearance of the second set of collections of microbes;
    b. determine one or more data properties of each of the collection of microbes in a third set of collections of microbes based at least in part upon the second data, wherein each collection of microbes in the third set is also in the second set;
    c. determine an expressed fitness level of each of the collections of microbes in the third set; and
    d. identify a second association between the determined one or more data properties and expressed fitness level of one or more of the collections of microbes in the third set.
63. The computer readable media of any one of embodiments 43-62, wherein the one or more desired data properties are based at least in part upon application of the identified association to a desired fitness level.
64. A computer-implemented method of predicting a fitness level of a collection of microbes, the method comprising:
    a. obtaining, by a computing device, data relating to the collection of microbes,
        i. wherein the data is related to appearance of the collection of microbes;
    b. determining, by a computing device, one or more data properties of the collection of microbes based at least in part upon the data; and
    c. determining, by a computing device, a predicted fitness level for the collection of microbes based at least in part upon an association relating the determined one or more data properties and the predicted fitness level.
65. The method of embodiment 64, wherein the collection of microbes includes only one microbe.
66. The method of embodiment 64, wherein the collection of microbes is a group of two or more microbes.
67. The method of embodiment 66, wherein the group contains less than or equal to 100 microbes.
68. The method of embodiment 64, wherein the collection of microbes is a microbe colony.
69. The method of embodiment 68, wherein the microbe colony contains more than 100 microbes.
70. The method of any one of embodiments 64-69, wherein microbes in the collection of microbes are from the same species.
71. The method of any one of embodiments 64-70, wherein microbes in the collection of microbes are isogenic.
72. The method of any one of embodiments 64-71, wherein the possible values of a data property are discrete.
73. The method of any one of embodiments 64-72, wherein the possible values of a data property are selected from a continuous range.

74. The method of any one of embodiments 64-73, wherein the data is image data and the one or more data properties are one or more image properties.

75. The method of embodiment 74, wherein the one or more image properties are: size, color, eccentricity, aspect ratio, opacity, edge roughness, edge sharpness, fluorescence, uniformity, topology, height, opacity profile, uniformity profile, fluorescence profile, height profile, distance to a nearest neighboring collection of microbes, growth rate, local density of the collections of microbes, or any combination thereof, wherein the local density of a collection of microbes is based at least in part upon one or more of: a predetermined radius about each collection of microbes, a size of each collection of microbes, or a predetermined number of collections of microbes surrounding each collection of microbes.

76. A system for predicting a fitness level of a collection of microbes, the system comprising:
   a. one or more processors; and
   b. one or more memories operatively coupled to at least one of the one or more processors and having instructions stored thereon that, when executed by at least one of the one or more processors, cause the system to:
      i. obtain data relating to the collection of microbes,
         1. wherein the data is related to appearance of the collection of microbes;
      ii. determine one or more data properties of the collection of microbes based at least in part upon the data; and
      iii. determine a predicted fitness level for the collection of microbes based at least in part upon an association relating the determined one or more data properties and the predicted fitness level.

77. The system of embodiment 76, wherein the collection of microbes includes only one microbe.

78. The system of embodiment 76, wherein the collection of microbes is a group of two or more microbes.

79. The system of embodiment 78, wherein the group contains less than or equal to 100 microbes.

80. The system of embodiment 76, wherein the collection of microbes is a microbe colony.

81. The system of embodiment 80, wherein the microbe colony contains more than 100 microbes.

82. The system of any one of embodiments 76-81, wherein microbes in the collection of microbes are from the same species.

83. The system of any one of embodiments 76-82, wherein microbes in the collection of microbes are isogenic.

84. The system of any one of embodiments 76-83, wherein the possible values of a data property are discrete.

85. The system of any one of embodiments 76-84, wherein the possible values of a data property are selected from a continuous range.

86. The system of any one of embodiments 76-85, wherein the data is image data and the one or more data properties are one or more image properties.

87. The system of embodiment 86, wherein the one or more image properties are: size, color, eccentricity, aspect ratio, opacity, edge roughness, edge sharpness, fluorescence, uniformity, topology, height, opacity profile, uniformity profile, fluorescence profile, height profile, distance to a nearest neighboring collection of microbes, growth rate, local density of the collections of microbes, or any combination thereof, wherein the local density of a collection of microbes is based at least in part upon one or more of: a predetermined radius about each collection of microbes, a size of each collection of microbes, or a predetermined number of collections of microbes surrounding each collection of microbes.

88. One or more computer readable media storing instructions for predicting a fitness level of a collection of microbes, wherein the instructions, when executed by one or more computing devices, cause at least one of the one or more computing devices to:
   a. obtain data relating to the collection of microbes,
      i. wherein the data is related to appearance of the collection of microbes;
   b. determine one or more data properties of the collection of microbes based at least in part upon the data; and
   c. determine a predicted fitness level for the collection of microbes based at least in part upon an association relating the determined one or more data properties and the predicted fitness level.

89. The computer readable media of embodiment 88, wherein the collection of microbes includes only one microbe.

90. The computer readable media of embodiment 88, wherein the collection of microbes is a group of two or more microbes.

91. The computer readable media of embodiment 90, wherein the group contains less than or equal to 100 microbes.

92. The computer readable media of embodiment 88, wherein the collection of microbes is a microbe colony.

93. The computer readable media of embodiment 92, wherein the microbe colony contains more than 100 microbes.

94. The computer readable media of any one of embodiments 88-93, wherein microbes in the collection of microbes are from the same species.

95. The computer readable media of any one of embodiments 88-94, wherein microbes in the collection of microbes are isogenic.

96. The computer readable media of any one of embodiments 88-95, wherein the possible values of a data property are discrete.

97. The computer readable media of any one of embodiments 88-96, wherein the possible values of a data property are selected from a continuous range.

98. The computer readable media of any one of embodiments 88-97, wherein the data is image data and the one or more data properties are one or more image properties.

99. The computer readable media of embodiment 98, wherein the one or more image properties are: size, color, eccentricity, aspect ratio, opacity, edge roughness, edge sharpness, fluorescence, uniformity, topology, height, opacity profile, uniformity profile, fluorescence profile, height profile, distance to a nearest neighboring collection of microbes, growth rate, local density of the collections of microbes, or any combination thereof, wherein the local density of a collection of microbes is based at least in part upon one or more of: a predetermined radius about each collection of microbes, a size of each collection of microbes, or a predetermined number of collections of microbes surrounding each collection of microbes.

The invention claimed is:

1. A computer-implemented method of identifying a collection of microbes based on fitness level, the method comprising:
obtaining, by a computing device, image data relating to a plurality of collections of microbes, wherein one or more of the collections of microbes have a different fitness level than at least one of the other collections of microbes, and the image data is related to appearance of the plurality of collections of microbes;
determining, by a computing device, one or more values of one or more image data properties of each of the collections of microbes in a first set of the plurality of collections of microbes based at least in part upon the image data, wherein at least one of the one or more image data properties is related to a size of the corresponding collection of microbes, and the first set comprises two or more collections of microbes;
determining an expressed value of the fitness level of each of the collections of microbes in the first set;
identifying an association between the one or more image data properties and the fitness level, across the collections of microbes in the first set, based at least in part upon the one or more values of the one or more image data properties and the corresponding expressed value of the fitness level for each collection of microbes in the first set; and
identifying a first collection of microbes based at least in part upon a predicted value of the fitness level, wherein the predicted value of the fitness level is based at least in part upon the association and one or more values of the one or more image data properties of the first collection of microbes.

2. The method of claim 1, wherein the fitness level is related to productivity.

3. The method of claim 2, wherein larger size is associated with higher productivity.

4. The method of claim 1, wherein the fitness level is related to yield.

5. The method of claim 4, wherein smaller size is associated with higher yield.

6. The method of claim 1, further comprising:
identifying that a second collection of microbes includes contaminating microbes based at least in part upon one or more values of one or more image data properties of the second collection of microbes.

7. The method of claim 1, further comprising:
selecting the first collection of microbes for further processing.

8. The method of claim 7, wherein the selected first collection of microbes comprises microbes with improved fitness relative to at least one collection of microbes in the plurality of collections of microbes.

9. The method of claim 7, wherein the selected first collection of microbes comprises microbes with reduced fitness relative to at least one collection of microbes in the plurality of collections of microbes.

10. The method of claim 7, further comprising:
genetically modifying a microbe from the selected first collection of microbes.

11. A system for identifying a collection of microbes based on fitness level, the system comprising:
one or more processors; and
one or more memories operatively coupled to at least one of the one or more processors and having instructions stored thereon that, when executed by at least one of the one or more processors, cause the system to:
obtain image data relating to a plurality of collections of microbes, wherein one or more of the collections of microbes have a different fitness level than at least one of the other collections of microbes, and the image data is related to appearance of the plurality of collections of microbes;
determine one or more values of one or more image data properties of each of the collections of microbes in a first set of the plurality of collections of microbes based at least in part upon the image data, wherein at least one of the one or more image data properties is related to a size of the corresponding collection of microbes, and the first set comprises two or more collections of microbes;
determine an expressed value of the fitness level of each of the collections of microbes in the first set;
identify an association between the one or more image data properties and the fitness level, across the collections of microbes in the first set, based at least in part upon the one or more values of the one or more image data properties and the corresponding expressed value of the fitness level for each collection of microbes in the first set; and
identify a first collection of microbes based at least in part upon a predicted value of the fitness level, wherein the predicted value of the fitness level is based at least in part upon the association and one or more values of the one or more image data properties of the first collection of microbes.

12. The system of claim 11, wherein the fitness level is related to productivity.

13. The system of claim 12, wherein larger size is associated with higher productivity.

14. The system of claim 11, wherein the fitness level is related to yield.

15. The system of claim 14, wherein smaller size is associated with higher yield.

16. The system of claim 11, wherein at least one of the one or more memories operatively coupled to at least one of the one or more processors has instructions stored thereon that, when executed by at least one of the one or more processors, cause the system to:
select the first collection of microbes for further processing.

17. One or more computer readable media storing instructions for identifying a collection of microbes based on fitness level, wherein the instructions, when executed by one or more computing devices, cause at least one of the one or more computing devices to:
obtain image data relating to a plurality of collections of microbes, wherein one or more of the collections of microbes have a different fitness level than at least one of the other collections of microbes, and the image data is related to appearance of the plurality of collections of microbes;
determine one or more values of one or more image data properties of each of the collections of microbes in a first set of the plurality of collections of microbes based at least in part upon the image data, wherein at least one of the one or more image data properties is related to a size of the corresponding collection of microbes, and the first set comprises two or more collections of microbes;
determine an expressed value of the fitness level of each of the collections of microbes in the first set;
identify an association between the one or more image data properties and the fitness level, across the collections of microbes in the first set, based at least in part upon the one or more values of the one or more image data properties and the corresponding expressed value of the fitness level for each collection of microbes in the first set; and identify a first collection of microbes based at least in part upon a predicted value of the fitness level, wherein the predicted value of the fitness level is based at least in part upon the association and one or more values of the one or more image data properties of the first collection of microbes.

18. The computer readable media of claim 17, wherein the fitness level is related to productivity, and larger size is associated with higher productivity.

19. The computer readable media of claim 17, wherein the fitness level is related to yield, and smaller size is associated with higher yield.

20. The computer readable media of claim 17, storing instructions that, when executed by the one or more computing devices, cause at least one of the one or more computing devices to:

select the first collection of microbes for further processing.

\* \* \* \* \*